US009061006B2

(12) United States Patent
Adler-Abramovich et al.

(10) Patent No.: US 9,061,006 B2
(45) Date of Patent: Jun. 23, 2015

(54) COMPOSITIONS AND METHODS FOR DIAGNOSING AND TREATING PHENYLKETONURIA (PKU)

(75) Inventors: Lihi Adler-Abramovich, Herzlia (IL); Ohad Carny, Kochav Yair (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/003,803

(22) PCT Filed: Mar. 8, 2012

(86) PCT No.: PCT/IL2012/050081
§ 371 (c)(1),
(2), (4) Date: Sep. 8, 2013

(87) PCT Pub. No.: WO2012/120518
PCT Pub. Date: Sep. 13, 2012

(65) Prior Publication Data
US 2013/0344079 A1 Dec. 26, 2013

Related U.S. Application Data

(60) Provisional application No. 61/450,148, filed on Mar. 8, 2011.

(51) Int. Cl.
| | | |
|---|---|---|
| *A61K 39/395* | (2006.01) | |
| *G01N 33/68* | (2006.01) | |
| *A61K 31/428* | (2006.01) | |
| *A61K 31/465* | (2006.01) | |
| *A61K 31/473* | (2006.01) | |
| *A61K 31/5415* | (2006.01) | |
| *A61K 31/65* | (2006.01) | |
| *A61K 31/655* | (2006.01) | |
| *A61K 45/06* | (2006.01) | |
| *C07K 16/44* | (2006.01) | |

(52) U.S. Cl.
CPC ............ *A61K 39/3955* (2013.01); *C07K 16/44* (2013.01); *G01N 33/6893* (2013.01); *G01N 2800/7047* (2013.01); *A61K 31/428* (2013.01); *A61K 31/465* (2013.01); *A61K 31/473* (2013.01); *A61K 31/5415* (2013.01); *A61K 31/65* (2013.01); *A61K 31/655* (2013.01); *A61K 45/06* (2013.01)

(58) Field of Classification Search
None
See application file for complete search history.

(56) References Cited

U.S. PATENT DOCUMENTS

2009/0035295 A1 2/2009 Hillen et al.

FOREIGN PATENT DOCUMENTS

| WO | WO 97/05906 | 2/1997 |
|---|---|---|
| WO | WO 2012/120518 | 9/2012 |

OTHER PUBLICATIONS

Adler-Abramovich et al., Phenylalanine assembly into toxic fibrils suggests amyloid etiology in phenylketonuria, Aug. 2012, Nature Chemical Biology 8:701-706.*
Bucciantini et al. "Inherent Toxicity of Aggregates Implies A Common Mechanism for Protein Misfolding Diseases", Nature, 416: 507-511, Apr. 4, 2002.
Chiti et al. "Protein Misfolding, Functional Amyloid, and Human Disease", Annual Review of Biochemistry, 75: 333-366, 2006.
Choi et al. "Phenylalanine Transport at the Human Blood-Brain Barrier", The Journal of Biological Chemistry, 261(14): 6536-6541, May 15, 1986.
Cohen et al. "Therapeutic Approaches to Protein-Misfolding Diseases", Nature, 426: 905-909, Dec. 18-25, 2003.
Cunningham "Phenylketonuria. Early Detection, Diagnosis and Treatment", California Medicine, XP002678184, 105(1): 1-7, Jul. 1966. p. 2.
Dobson "Protein Misfolding, Evolution and Disease", Trends in Biochemistry Science, TIBS, 24: 329-332, Sep. 1999.
Findeis et al. "Modified-Peptide Inhibitors of Amyloid ?-Peptide Polymezation", Biochemistry, 38(21): 6791-6800, 1999.
Gazit "A Possible Role for Pi-Stacking in the Self-Assembly of Amyloid Fibrils", The FASEB Journal, XP002678186, 16: 77-83, Feb. 1, 2000. p. 77-78.
Hanley "Adult Phenylketonuria", American Journal of Medicine, 117: 590-595, 2004.
Harper et al. "Models of Amyloid Seeding in Alzheimer's Disease and Scrapie: Mechanistic Truths and Physiological Consequences of the Time-Dependent Solubility of Amyloid Proteins", Annual Review of Biochemistry, 66: 385-407, 1997.
Krause et al. "Biochemical and Neuropsychological Effects of Elevated Plasma Phenylalanine in Patients With Treated Phenylketonuria. A Model for the Study of Phenylalanine and Brain Function in Man", Journal of Clinical Investigation, 75: 40-48, Jan. 1985.
Leandro et al. "Phenylketonuria as a Protein Misfolding Disease: The Mutation PG46S in Phenylalanine Hydroxylase Promotes Self-Association and Fibril Formation", Biochimica et Biophysica Acta, XP002678185, 1812: 106-120, Oct. 16, 2010. Abstract, p. 116, Para 4.3, Fig. 9E.

(Continued)

*Primary Examiner* — John Ulm

(57) ABSTRACT

A method of diagnosing Phenylketonuria (PKU) in a subject in need thereof is disclosed. The method comprises detecting phenylalanine fibrils in a tissue of the subject, wherein a presence or level above a predetermined threshold of said phenylalanine fibrils in said tissue, is indicative of PKU in the subject. Antibodies capable of detecting phenylalanine fibrils are also disclosed as well as additional uses.

4 Claims, 11 Drawing Sheets
(6 of 11 Drawing Sheet(s) Filed in Color)

(56) References Cited

OTHER PUBLICATIONS

Pawar et al. "Prediction of 'Aggregation-Prone' and 'Aggregation-Susceptible' Regions in Proteins Associated With Neurodegenerative Diseases", Journal of Molecular Biology, JMB, 350: 379-392, 2005.
Reches et al. "Amyloid Fibril Fromation by Pentapeptide and Tetrapeptide Fragments of Human Calcitonin", The Journal of Biological Chemistry, 277(38): 35475-35480, Sep. 20, 2002.
Reches et al. "Casting Metal Nanowires Within Discrete Self-Assembled Peptide Nanotubes", Science, XP002276672, 300(5619): 625-627, Apr. 25, 2003.
Scriver "The PAH Gene, Phenylketonuria, and A Paradigm Shift", Human Mutation, 28(9): 831-845, 2007.
Shedlovsky et al. "Mouse Models of Human Phenylketonuria", Genetics, XP002678183, 134: 1205-1210, Aug. 1993. p. 1206, r-h Col., Last Para—p. 1207, r-h Col., 1st Full Para.
Sipe et al. "Review: History of the Amyloid Fibril", Journal of Structural Biology, 130: 88-98, 2000.
Sunde et al. "From the Globular to the Fibrous State: Protein Structure and Structural Conversion in Amyloid Formation", Quaterly Reviews of Biophysics, 31(1): 1-39, 1998.
Surtees et al. "The Neurochemistry of Phenylketonuria", European Journal of Pediatry, 159(Suppl.2): S109-S113, 2000.
Tjernberg et al. "Arrest of ?-Amyloid Fibril Formation by a Pentapeptide Ligand", The Journal of Biological Chemistry, 271(15): 8545-8548, Apr. 12, 1996.
Yamamoto et al. "Reversal of Subjective Temporal Order Due to Arm Crossing", Nature Neuroscience, 4(7): 759-765, Jul. 2001.

* cited by examiner

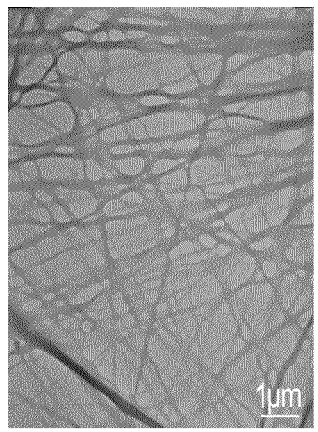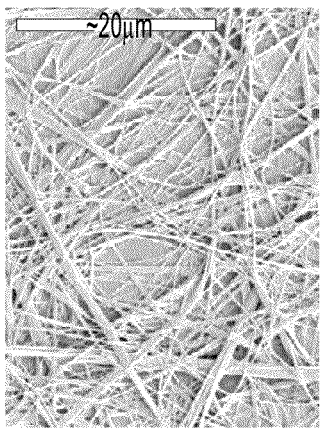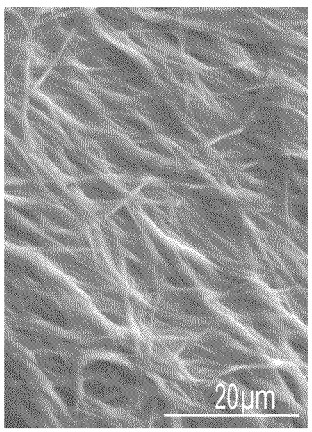
FIG. 1A   FIG. 1B   FIG. 1C
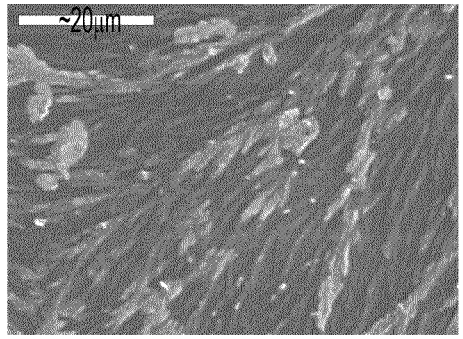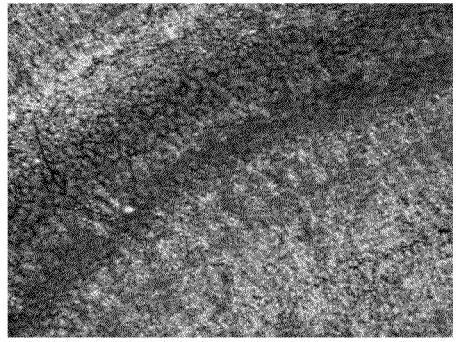
FIG. 1D   FIG. 1E
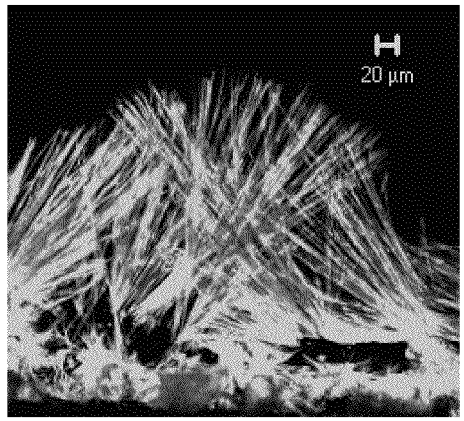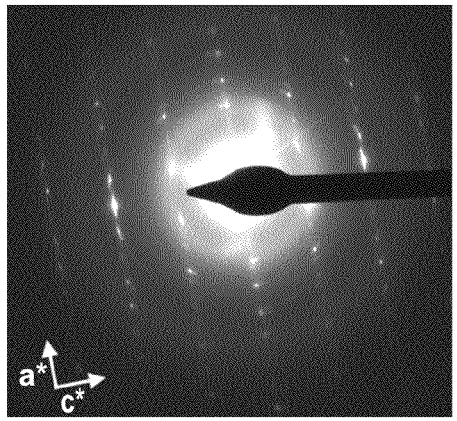
FIG. 1F   FIG. 1G

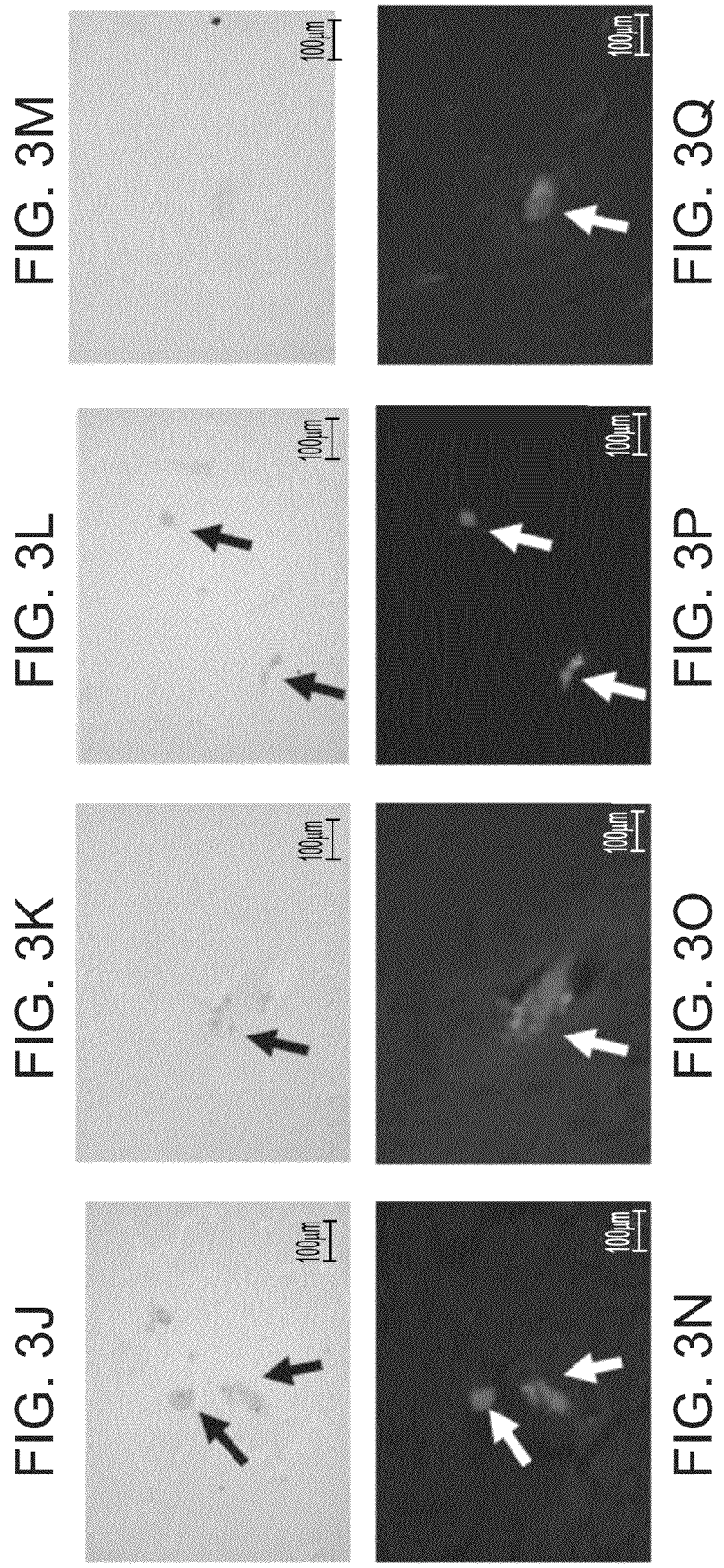

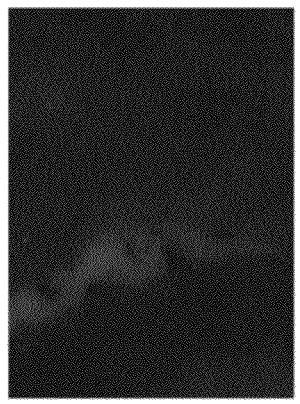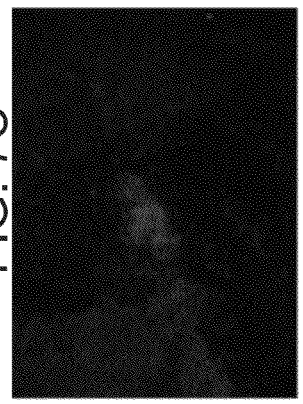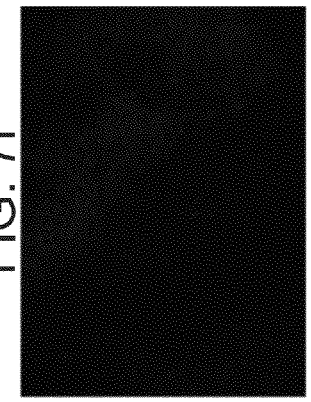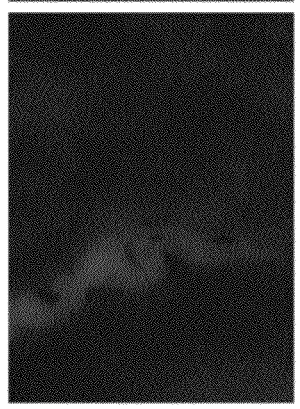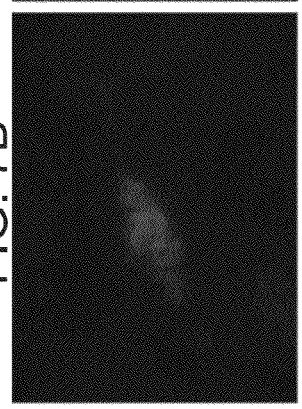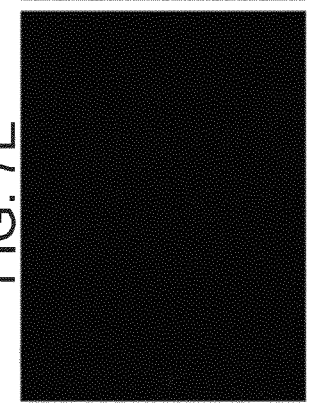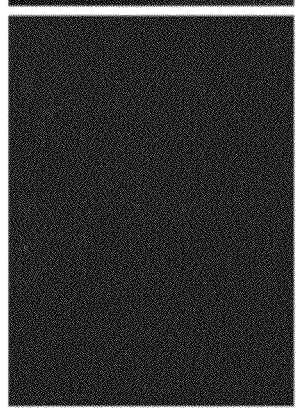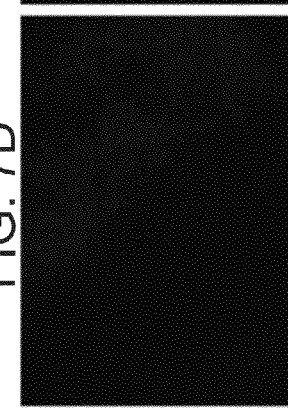

COMPOSITIONS AND METHODS FOR DIAGNOSING AND TREATING PHENYLKETONURIA (PKU)

RELATED APPLICATIONS

This application is a National Phase of PCT Patent Application No. PCT/IL2012/050081 having International filing date of Mar. 8, 2012, which claims the benefit of priority under 35 USC §119(e) of U.S. Provisional Patent Application No. 61/450,148 filed on Mar. 8, 2011. The contents of the above applications are all incorporated by reference as if fully set forth herein in their entirety.

FIELD AND BACKGROUND OF THE INVENTION

Embodiments of the present invention relate to compositions and methods for diagnosing and treating Phenylketonuria (PKU).

By a mechanism not completely understood, PKU patients suffer from mental retardation, epilepsy, organ damage, unusual posture and, in cases of maternal PKU, severely compromised pregnancy. Classical PKU is an autosomal recessive disorder, caused by mutations in the PAH gene, located on chromosome 12. Mutations in both alleles of the gene result in remarkably high concentrations of phenylalanine[2, 3]. Excessive phenylalanine is partly metabolized into phenylketones by transamination, however in untreated patients millimolar concentrations of phenylalanine can accumulate in the plasma, cerebrospinal fluid (CSF) and brain tissue[5, 6]. Inclusion of PKU diagnosis to newborn screening programs, by semiquantitative methods such as the Guthrie test or modern analytical tools to measure the blood levels of phenylalanine, allows early diagnosis of affected patients. This permits treatment with phenylalanine-restricted diet before clinical symptoms appear. In adults who do not keep a strict diet there is a risk of late motor and cognitive decline[3]. In most of the previous studies phenylalanine is considered to be the main neurotoxin, although the precise mechanism underlying the neurologic affect still needs to be deciphered[3].

In the past decade, the role of peptide and protein aggregation in many pathological disorders was revealed. Specific attention was drawn to the formation of ordered amyloid fibrils. It was clearly demonstrated that amyloid fibrils or their early intermediates are associated with a diverse group of diseases of unrelated origin, including Alzheimer's disease, Type II diabetes, and prion disorders. Despite their formation by a diverse and structurally unrelated group of proteins, all amyloid fibrils share similar biophysical and structural properties[4, 7-12].

A very intriguing point is the fact that very short peptide fragments, as short as penta- and tetra-peptides, can form typical amyloid fibrils that share the same biophysical and structural properties of the assemblies formed by much larger polypeptides[13, 14]. Furthermore, it was demonstrated that a diphenylalanine peptide spontaneously forms well ordered nano-tubular assemblies by itself, with some amyloid-like structural signatures[18]. This short peptide represents the core recognition motif within the β-amyloid polypeptide, which forms amyloid plaques in the case of Alzheimer's disease. The two phenylalanine residues (Phe19, Phe20), in the β-amyloid polypeptide, are suggested to mediate the intermolecular interaction between polypeptide chains, further substantiated by being a key component of peptide-based inhibitors of β-amyloid fibril formation[15-17].

A variety of structural and biophysical studies indicate the role of interactions between aromatic residues in amyloidogenic process acceleration and amyloidal structure stabilization. While aromatic interactions are not crucial for the process of amyloid formation they can significantly accelerate the process, affect the morphology of the assemblies, and reduce the minimal association concentrations[13, 19-22].

To date, PKU has not been associated with amyloid-like fibrillar load.

SUMMARY OF THE INVENTION

According to one aspect of the present invention there is provided a method of diagnosing Phenylketonuria (PKU) in a subject in need thereof, the method comprising detecting phenylalanine fibrils in a tissue of the subject, wherein a presence or level above a predetermined threshold of the phenylalanine fibrils in the tissue, is indicative of PKU in the subject.

According to one aspect of the present invention there is provided an isolated antibody which specifically binds to fibrils consisting of phenylalanine.

According to one aspect of the present invention there is provided a pharmaceutical composition comprising as an active ingredient the isolated antibody described herein.

According to one aspect of the present invention there is provided a method of detecting phenylalanine fibrils in a biological sample, the method comprising contacting the biological sample with the antibody described herein under conditions which allow formation of immunocomplexes, wherein a presence of immunocomplexes above a predetermined threshold is indicative of phenylalanine fibrils in the biological sample.

According to one aspect of the present invention there is provided a method of treating PKU in a subject in need thereof, the method comprising administering to the subject a therapeutic effective amount of an anti-amyloid agent, thereby treating the PKU in the subject.

According to one aspect of the present invention there is provided a composition of matter comprising fibrils of phenylalanine.

According to still further features in the described preferred embodiments the detecting is effected using an isolated antibody which specifically binds to fibrils consisting of phenylalanine.

According to still further features in the described preferred embodiments the detecting is effected with a dye.

According to still further features in the described preferred embodiments the dye is selected from the group consisting of Congo red and ThT.

According to still further features in the described preferred embodiments the antibody is attached to an identifiable moiety.

According to still further features in the described preferred embodiments the antibody is a polyclonal antibody.

According to still further features in the described preferred embodiments the antibody is a monoclonal antibody.

According to still further features in the described preferred embodiments the anti-amyloid agent is selected from the group consisting of a small molecule and an antibody.

According to still further features in the described preferred embodiments the method further comprises administering to the subject a therapeutically effective amount of an NSAID.

According to still further features in the described preferred embodiments the small molecule is selected from the group consisting of nicotine, acridine, acridine orange, methylene blue, congo red, thioflavin-T and tetracycline.

According to still further features in the described preferred embodiments the fibrils have a minimal diameter of 10 nm and a maximal diameter of 5000 nm.

According to still further features in the described preferred embodiments the fibrils bind a small molecule selected from the group consisting of congo red and thioflavin-T.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1H:
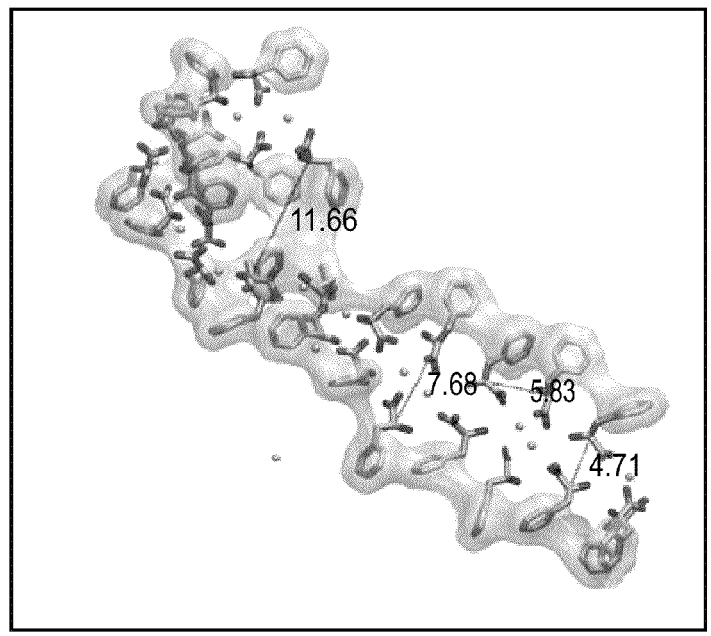
Figure 1I:
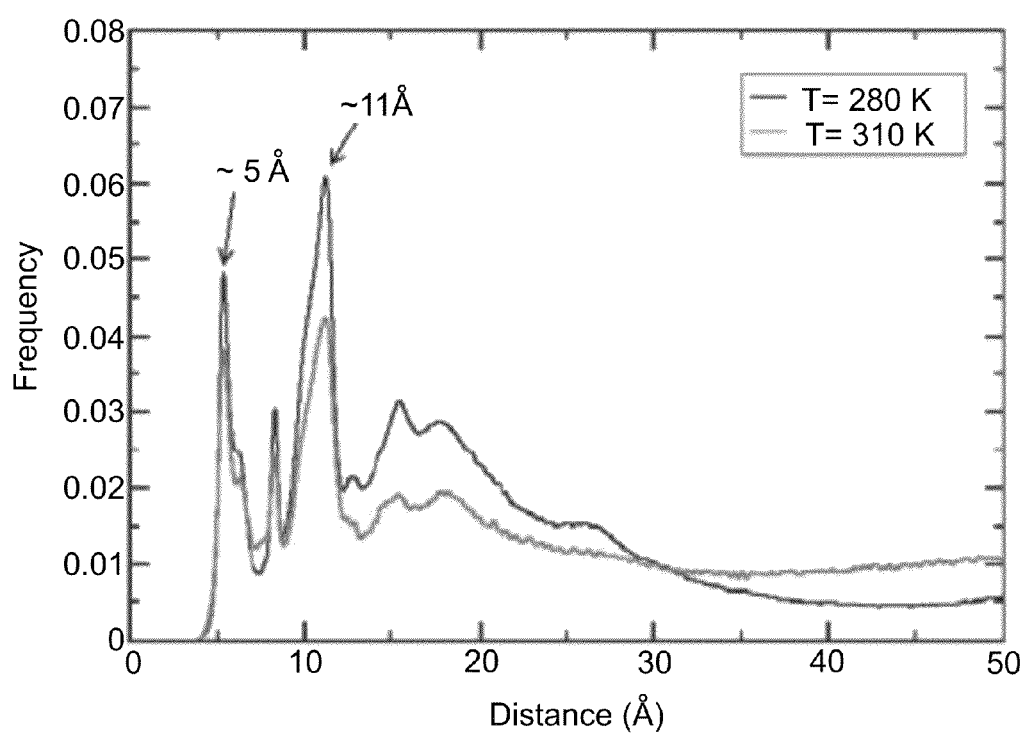
Figure 1J:
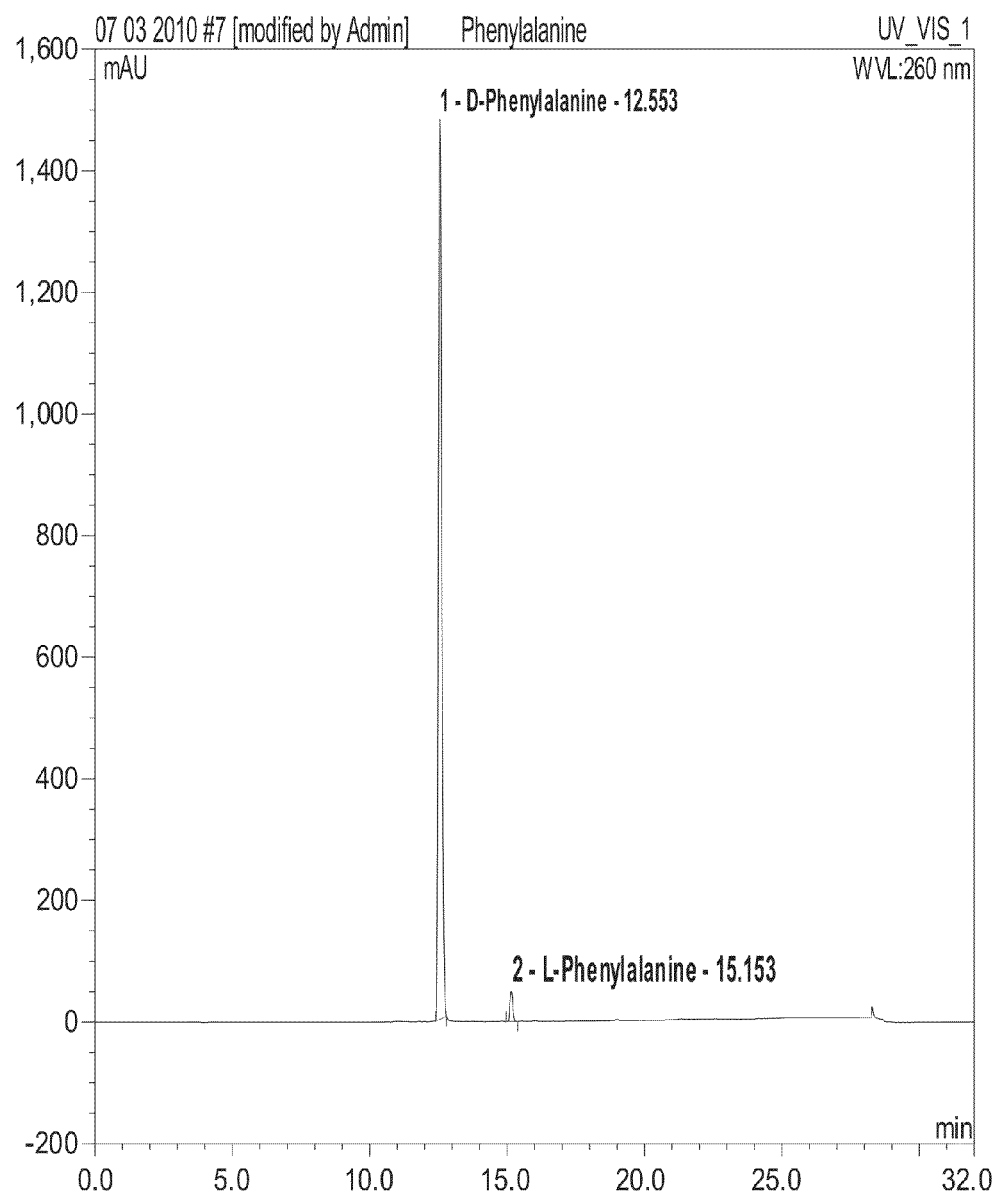
Figure 1K:
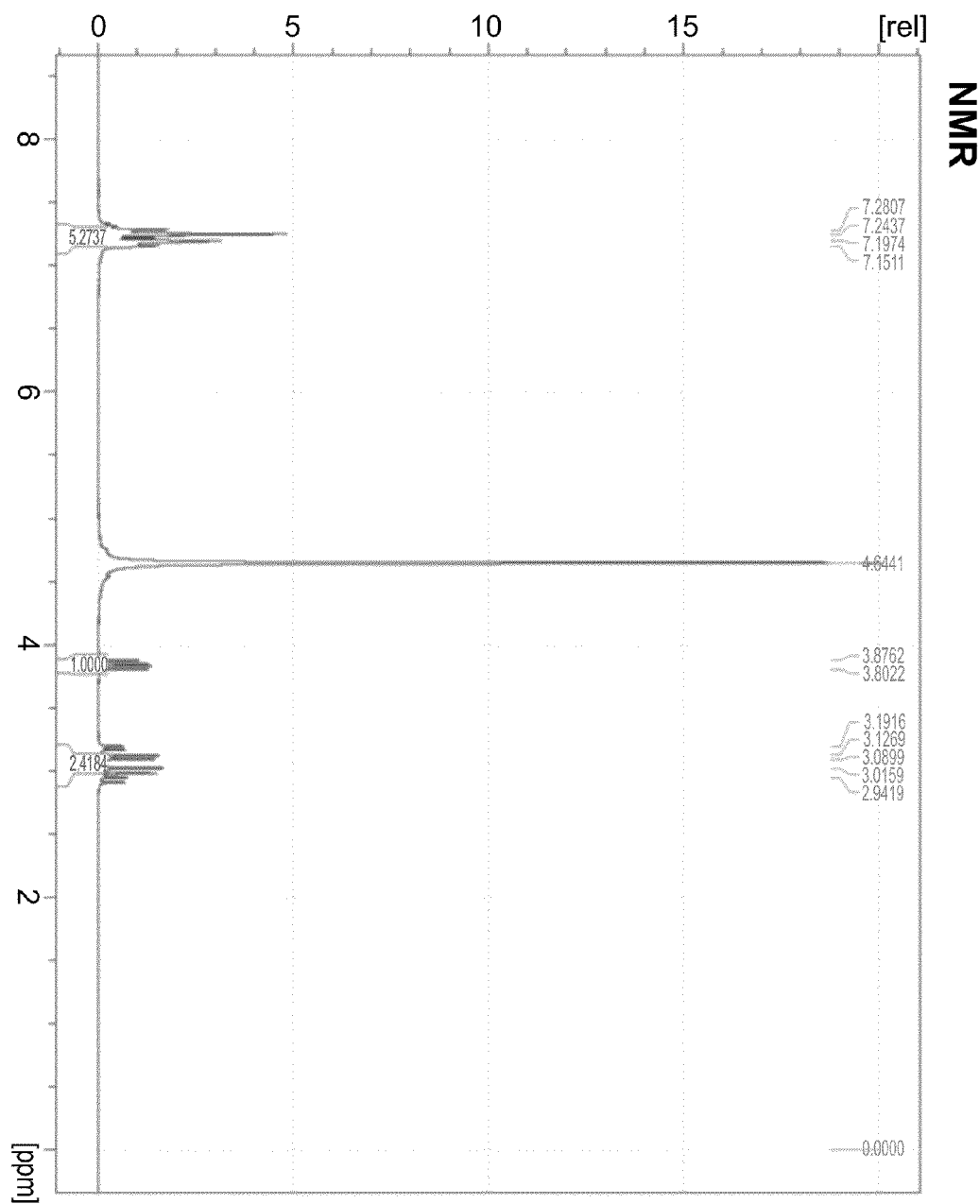

FIGS. 1A-K are images and graphs illustrating that the single aromatic amino acid, phenylalanine, self assembles into supramolecular fibrillar structures. (A) Transmittance electron microscopy images of elongated phenylalanine fibrils. (B) Scanning electron microscopy (SEM) image of the phenylalanine fibrils. (C) Environmental scanning electron microscopy image of the phenylalanine fibrils. (D) SEM images of phenylalanine fibrils in human serum. (E) Microscopic examination under polarized light following CR staining of phenylalanine fibrils. (F) Confocal microscopy image of fibrils dyed with Thioflavin T (ThT). (G) Electron-diffraction analysis of a single fibril. Axis a* is oriented normal to the long axis of the crystal. a* and c* are the reciprocal lattice vectors in the diffraction pattern. (H) Representative snapshot of the filamentous structure obtained by molecular dynamics simulations started from 27 monodisperse phenylalanine molecules (cyan) at high pH in the presence of counterions (yellow spheres). The tight packing of the aromatic rings is emphasized by their van der Waals envelope (gray surface). (I) Distribution of distances between pairs of atoms in different phenylalanine molecules in the aggregates obtained by molecular dynamics simulations. The distances between all pairs of center of masses of the 27 phenylalanines were employed for these histograms, and quantitatively similar histograms are obtained using distances between atoms instead of center of masses. The very similar distributions at 280 K (black) and 310 K (red) show that the ordered aggregates of Phe are essentially the same in this temperature range, and that the simulations have reached convergence. FIGS. 1J-K illustrate NMR (J) and HPLC (K) analysis of phenylalanine assemblies indicating that no covalent bonds between the phenylalanine monomers were formed.

FIGS. 2A-F are graphs and images illustrating the toxic effect of phenylalanine fibrillar structures on cells. Cell viability was determined using the MTT assay. (A) CHO cell line was maintained in the absence or presence of increasing amount of phenylalanine fibrils. (B-C) Scanning electron microscopy (SEM) images of untreated CHO cells. (D-E) SEM image of CHO cells incubated with phenylalanine fibrils. (F) PC 12 cell line was maintained in the presence of increasing amount of phenylalanine fibrils (black bars) or an increasing amount of the control amino acid, alanine (gray bars).

Figure 3A:
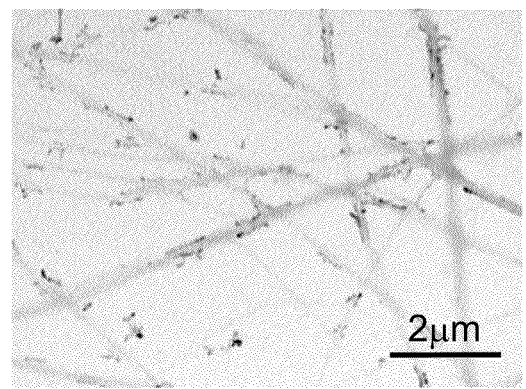

FIGS. 3A-Q: Specific antibodies against phenylalanine fibrils. (A) Transmittance electron micrographs of immuno-gold phenylalanine fibrils, antibodies were specifically bind to phenylalanine fibrils, and then marked with a seconded antibody conjugated to 18 nm gold particles. (B) Cell viability was determined using the MTT assay, CHO cell line was maintained in the presence of increasing amount of phenylalanine fibrils (black bars) or immuno-precipitated solutions of phenylalanine depleted of fibrils (gray bars). (C) Dot-blot analysis of phenylalanine fibrils, column 1, serum of homozygote mouse (pah$^{enu2}$) strongly binds to the phenylalanine fibrils. Column 2, serum of heterozygote mouse (pah$^{enu2}$) did not bind to the phenylalanine fibrils. Column 3, serum of wild type mouse did not bind to phenylalanine fibrils. (D, G) Histological staining of homozygous pah$^{enu2}$ mice brain, the 20 μm thick brain slices were stained with specific rabbit anti-Phe fibril antibodies and (E, H) Congo red, then examined using fluorescent microscopy. (F, I) The detected amyloid-like plaques showed co-localization of fluorescent signal obtained from Congo red and antibody staining. Sections D, E, F demonstrate plaques in dentate gyrus, sections G, H, I show plaque presence in blood vessel close to hippocampus. (J, K, L) Phenylketonuria patient brain was stained with anti-Phe fibril serum, or with pre-immune serum (M) and examined using light microscopy. (N, O, P, Q) Phenylketonuria patient brain was stained with Congo red. Phenylalanine positive depositions were found in the parietal cortex (Scale bar for J-Q is 100 μm).

Figure 4:
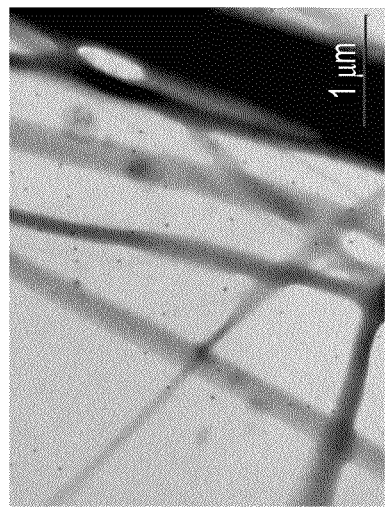

FIG. 4 is a transmission electron microscopy micrograph of phenylalanine fibrils marked only with a seconded antibody conjugated to 18 nm gold particles, this control sample does not show specific binding to the fibril due to the absence of the immunized serum.

Figure 5:
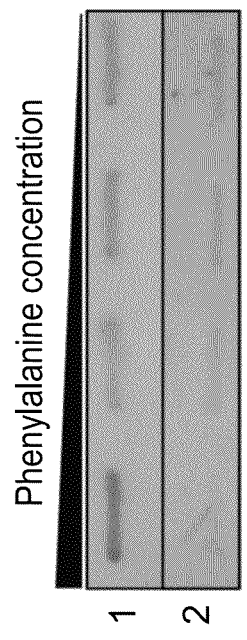

FIG. 5 is a slot blot binding analysis of the serum to phenylalanine fibrils. Serum from immunized rabbit was bound to the fibrils; first row represents the specific binding of the antibodies to the phenylalanine fibrils at decreasing concentrations (left to right). Second row represents the inability of the pre-immune serum to bind to phenylalanine fibrils.

Figure 6:
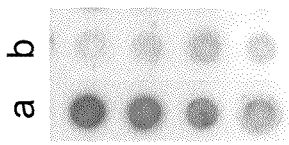

FIGS. 6A-B is a Dot-blot binding analysis of the serum to phenylalanine fibrils and diphenylalanine peptide nanotubes. (A) Serum from immunized rabbit was bound to the phenylalanine fibrils and demonstrated the specific binding of the serum antibodies to the phenylalanine fibrils at decreasing concentrations (top to bottom row). (B) Serum from immunized rabbit was bound to diphenylalanine peptide nanotubes, and demonstrated the inability of the antibodies to bind to the peptide nanotubes at all concentrations (decreasing top to bottom row).

FIGS. 7A-I are histological staining of homozygous and heterozygous pah$^{enu2}$ mice brain. The 20 μm thick brain slices were (A) stained with immunized serum that was antibody depleted (B) stained with antibodies from pre-immuned serum (C) heterozygous mouse brain stained with immunized serum (D, E, F) stained with Congo red, then examined using fluorescent microscopy. (G, H, I) co-localization of fluorescent signal obtained from Congo red and antibody staining. All images do not show any specific staining.

DESCRIPTION OF EMBODIMENTS OF THE INVENTION

The present invention, in some embodiments thereof, relates to compositions and methods for diagnosing and treating Phenylketonuria (PKU).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

A variety of structural and biophysical studies indicate that aromatic residues are important in the amyloidogenic process acceleration and amyloidal structure stabilization. While aromatic interactions are not crucial for the process of amyloid formation, they can significantly accelerate the process, affect the morphology of the assemblies, and reduce the minimal association concentrations. It was previously shown that very short aromatic peptide fragments, as short as penta- and tetra-peptides, can form typical amyloid fibrils which share the same biophysical and structural properties of the assemblies formed by much larger polypeptides. Furthermore, diphenylalanine peptide was shown to form well ordered nano-tubular assemblies by itself, with some amyloid-like structural signatures. This short peptide represents the core recognition motif within the β-amyloid polypeptide, which forms amyloid plaques in Alzheimer's disease. The two phenylalanine residues (Phe19, Phe20), in the β-amyloid peptide, were suggested to mediate the intermolecular interaction between polypeptide chains, a suggestion which was further substantiated by the use of phenylalanine residues as a key component of peptide-based inhibitors of β-amyloid fibril formation.

The present inventors examined the ability of the aromatic amino acid phenylalanine, to form ordered assemblies under pathologically-relevant concentrations. It was observed that phenylalanine by itself, at millimolar concentrations, self assembles to form amyloid-like nano-fibrillar structures with amyloid-like morphology and well-ordered electron diffraction (FIGS. 1A-K). These assemblies are specifically recognized by antibodies, show cytotoxicity that could be neutralized by the antibodies (FIG. 3B) and are present in the hippocampus of model mice (FIGS. 3C-I) and in parietal cortex of brain tissue of PKU patient (FIGS. 3J-Q). This is the first demonstration ever that a single amino acid can form amyloid-like deposits and suggests a novel amyloidosis-like etiology for phenylketonuria.

Thus, according to one aspect of the present invention, there is provided an isolated antibody which specifically binds to fibrils consisting of phenylalanine.

As used herein "phenylalanine fibrils" refers to fibrillar structures which are formed by the self-assembly of phenylalanine, when present in a tissue as a single amino acid. The self-assembly is probably mediated by π-stacking interactions, which also takes place in the process of amyloid formation.

The term "fibril" as used herein refers to a thread-like filamentous structure composed of higher ordered aggregates which is typically visible in an electron microscope.

Typically the phenylalanine fibrils have a minimal diameter of 10 nm and a maximal diameter of 5000 nm. Further the inventors have shown that the phenylalanine fibrils are capable of binding to small molecule dyes such as congo red and thioflavin-T.

The phenylalanine fibrils of this aspect of the present invention can be generated by dissolving phenylalanine in an aqueous medium (e.g. water or PBS) at a concentration between 1-200 mM.

Antibody agents of the present invention are capable of specifically binding the phenylalanine fibrils.

According to a particular embodiment the antibodies of the present invention bind to the phenylalanine fibrils with a Kd of about $10^7$-$10^{10}$.

The antibodies of this aspect of the present invention preferably bind with at least a 5 fold higher affinity (more preferably at least a 10 fold higher affinity) to phenylalanine fibrils than other fibrillar structures—e.g. α-synuclein amyloid deposits or diphenylalanine peptide nanotubes (see FIGS. 6A-B). As used herein, the term "antibody" refers to a substantially intact antibody molecule or an antibody fragment.

The phrase "isolated antibody" refers to an antibody which has been removed from its natural environment. For example, the present inventors have isolated anti-Phe fibril antibodies using a dot-blot assay (see FIG. 3C).

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

Methods for producing and screening for specific antibodies using hybridoma technology are routine and well known in the art. In a non-limiting example, mice can be immunized with the fibrils of the present invention. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding the fibrils of the invention. Ascites fluid, which generally contains high levels of antibodies can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with the fibrils of the invention with myeloma cells and then screening the hybridomas resulting from the fusion for hybridoma clones that secrete an antibody able to bind the fibrils.

Antibodies also can be generated in vitro, e.g., using recombinant antibody binding site expressing phage display libraries, in addition to the traditional in vivo methods using animals. See, e.g., Huse Science 246:1275 (1989); Ward Nature 341:544 (1989); Hoogenboom Trends Biotechnol. 15:62-70 (1997); Katz Annu. Rev. Biophys. Biomol. Struct. 26:27-45 (1997).

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in E. coli or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of Escherichia coli. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy or diagnostics, humanized antibodies are preferably used. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunisation. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

According to one embodiment, the antibodies of this aspect of the present invention are attached to an identifiable moiety.

The identifiable moiety can be a label which is directly visualized (e.g., a fluorescent molecule, a radioactive molecule) or a member of a binding (affinity) pair, which is identifiable via its interaction with an additional member of the binding pair (e.g., antibody-antigen pairs, enzyme-substrate pairs). Table 1, hereinbelow, provides examples of sequences of identifiable moieties.

TABLE 1

| Identifiable Moiety | Amino Acid sequence (Genebank Accession No.) | Nucleic Acid sequence (Genebank Accession No.) |
| --- | --- | --- |
| Green Fluorescent protein | AAL33912 | AF435427 |
| Alkaline phosphatase | AAK73766 | AY042185 |
| Peroxidase | NP_568674 | NM_124071 |
| Histidine tag | AAK09208 | AF329457 |
| Myc tag | AF329457 | AF329457 |
| Biotin lygase tag | NP_561589 | NC_003366 |
| orange fluorescent protein | AAL33917 | AF435432 |
| Beta galactosidase | NM_125776 | NM_125776 |
| Fluorescein isothiocyanate | AAF22695 | AF098239 |
| Streptavidin | S11540 | S11540 |

According to some embodiments of the invention, the therapeutic or identifiable moieties are conjugated by translationally fusing the polynucleotide encoding the antibody of the invention with the nucleic acid sequence encoding the therapeutic of identifiable moiety.

Additionally or alternatively, the therapeutic or identifiable moieties can be chemically conjugated (coupled) to the antibody of the invention, using any conjugation method known to one skilled in the art. For example, a peptide can be conjugated to an antibody of interest, using a 3-(2-pyridyldithio) propionic acid N-hydroxysuccinimide ester (also called N-succinimidyl 3-(2-pyridyldithio)propionate) ("SDPD") (Sigma, Cat. No. P-3415; see e.g., Cumber et al. 1985, Methods of Enzymology 112: 207-224), a glutaraldehyde conjugation procedure (see e.g., G. T. Hermanson 1996, "Antibody Modification and Conjugation", in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

Figure 3B:
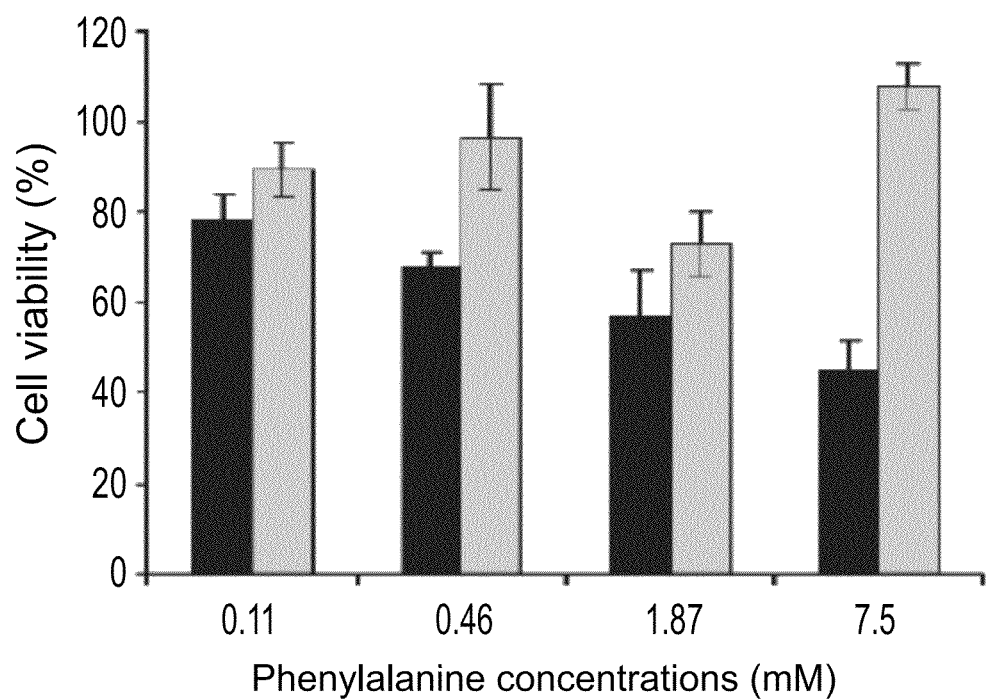
Figure 3C:
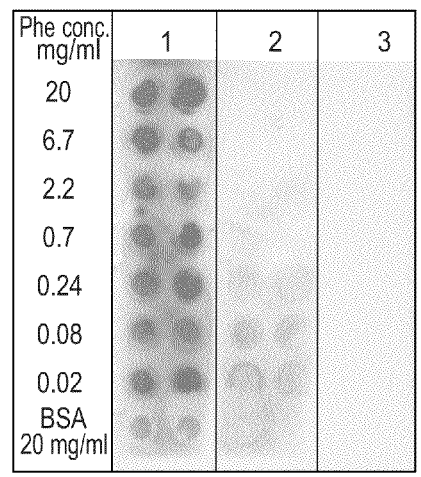
Figure 3D:
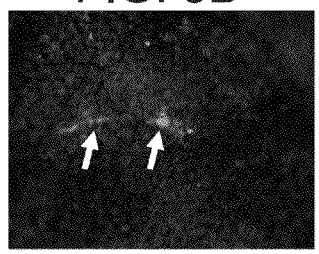
Figure 3E:
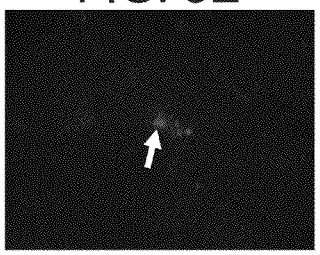
Figure 3F:
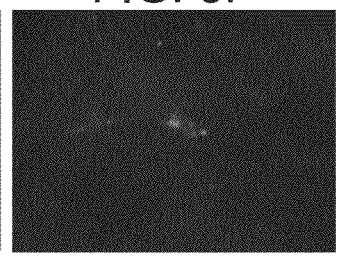
Figure 3G:
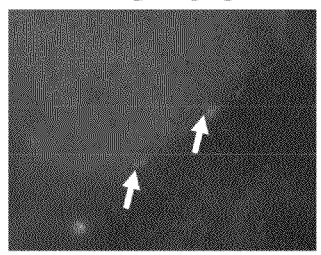
Figure 3H:
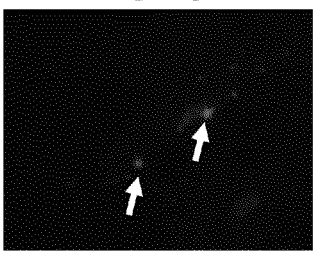
Figure 3I:
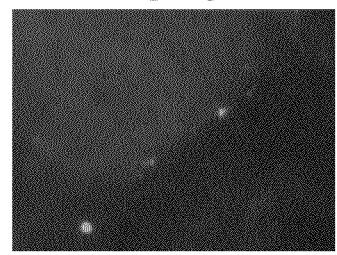

As shown in FIG. 3C, the antibodies described herein may be used to detect phenylalanine fibrils in a biological sample.

Thus, according to another aspect of the present invention there is provided a method of detecting phenylalanine fibrils in a biological sample, the method comprising contacting the biological sample with the antibodies described herein under conditions which allow formation of immunocomplexes, wherein a presence of immunocomplexes above a predetermined threshold is indicative of phenylalanine fibrils in the biological sample.

Depending on the particular antibody used and the concentration thereof, conditions may be selected which allow for the antibody to bind to the fibrils in the biological sample (e.g. osmolarity of the binding solution, temperature of the assay, during of the assay etc.).

Exemplary biological samples include tissue samples, cell samples and biological fluids (including cerebrospinal fluid, blood, urine, plasma, sweat, saliva).

According to one embodiment, the method is effected in vivo.

According to another embodiment, the method is effected ex vivo.

According to yet another embodiment, the method is effected in vitro (e.g. cell lines).

The present inventors have shown that the disease Phenylketonuria (PKU) is associated with the presence of phenylalanine fibrils. Specifically, the present inventors have demonstrated the presence of these fibrils in the parietal cortex of brain tissue of PKU patients (FIGS. 3J-Q).

Thus, according to yet another aspect of the present invention there is provided a method of diagnosing Phenylketonuria (PKU) in a subject in need thereof, the method comprising detecting phenylalanine fibrils in a tissue of the subject, wherein a presence or level above a predetermined threshold of the phenylalanine fibrils in the tissue, is indicative of PKU in the subject.

The disease Phenylketonuria (PKU) is associated with increased levels of phenylalanine. PKU patients suffer from a wide range of symptoms include mental retardation, epilepsy, organ damage, unusual posture and, in cases of maternal PKU, severely compromised pregnancy. Classical PKU is an autosomal recessive disorder, caused by mutations in the PAH gene, located on chromosome 12.

As used herein the phrase "diagnosing" refers to classifying a pathology, determining a severity of the pathology, monitoring pathology progression (with or without treatment), forecasting an outcome of a pathology and/or prospects of recovery. Alternatively or additionally, the term also encompasses determining treatment regimen, whereby fibrils are detected in accordance with the present teachings, and the subject is treated accordingly (e.g., such as by administering anti amyloid agents, as described herein).

As used herein "above a predetermined threshold" refers to phenylalanine fibril levels which are above those found in a control sample (of the same type) of a PKU unaffected subject. According to some embodiments of the invention, screening of the subject for PKU is followed by substantiation of the screen results using gold standard methods (e.g. Guthrie test or using analytical tools to measure the blood levels of phenylalanine or analyzing the DNA sequence of the PAH gene).

Detecting phenylalanine fibrils in a tissue of the subject (e.g., brain) may be effected using an antibody (e.g. those described herein above) or a dye.

Exemplary dyes that have been shown to bind to phenylalanine fibrils include congo red and thioflavin-T.

The agents of some embodiments of the invention which are described hereinabove for detecting PKU may be included in a diagnostic kit/article of manufacture preferably along with appropriate instructions for use and labels indicating FDA approval for use in diagnosing and/or assessing PKU.

Such a kit can include, for example, at least one container including at least one of the above described diagnostic agents (e.g., dye or anti phenylalanine fibril antibody)) and an imaging reagent packed in another container (e.g., enzymes, secondary antibodies, buffers, chromogenic substrates, fluorogenic material). The kit may also include appropriate buffers and preservatives for improving the shelf-life of the kit.

As mentioned, the present inventors have shown that down-regulation of phenylalanine fibrils using antibodies directed there against reduce their cytotoxicity (FIG. 3B). Accordingly, the present inventors propose that agents which down-regulate amyloids may be used to treat PKU.

Thus, according to still another aspect of the present invention, there is provided a treating PKU in a subject in need thereof, the method comprising administering to the subject a therapeutic effective amount of an anti-amyloid agent, thereby treating the PKU in the subject.

As used herein the phrase "anti amyloid agent" refers to an agent which is capable of inhibiting amyloid aggregate formation or disrupting pre-assembled amyloid aggregates [see e.g., Gazit, E. (2002) Curr. Med. Chem. 9: 1725-1735; Sacchettini (2002) Nat Rev Drug Discov 1:267-275].

The present invention contemplates both proteinaceous and non-proteinaceous anti amyloid agents.

An example of a proteinaceous anti-amyloid agent is an antibody, such as those described herein above.

Below is a summary of non-proteinaceous anti-amyloid agents that may be used to treat PKU.

Non-Proteinaceous Agents

Numerous non-proteinaceous agents are known in the art as anti-amyloid agents. Typically, such compositions are of an aromatic nature, as explained hereinabove.

One example of a group of compounds which can be used in accordance with the present invention is phenol-containing compounds (see for example, PCT Publication No. WO 2005/027901) such as having the general Formula I:

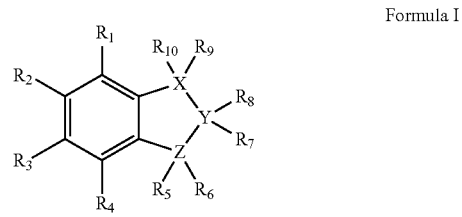

Formula I a pharmaceutically acceptable salt thereof or a prodrug thereof, wherein:

X, Y and Z are each independently selected from the group consisting of carbon, oxygen, sulfur, $CR_{11}R_{12}$ or $R_{13}R_{14}C$—$CR_{15}R_{16}$, provided that at least one of X, Y and Z is oxygen or sulfur;

$R_1$-$R_{16}$ are each independently selected from the group consisting of hydrogen, lone pair electrons, hydroxy, alkyl, cycloalkyl, phenyl, alkoxyphenyl, thioalkoxyphenyl, aryloxyphenyl, thioaryloxyphenyl, carboxyphenyl, thiocarboxyphenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$-$R_4$ and/or at least two of $R_5$-$R_{16}$ form at least one five- or six-membered aromatic, heteroaromatic, alicyclic or heteroalicyclic ring, whereas:

at least one of $R_1$-$R_4$ is selected from the group consisting of hydroxy, alkoxy, aryloxy, thiohydroxy, thioalkoxy, thioaryloxy, O-carboxy and O-thiocarboxy; and/or at least one of $R_5$-$R_{16}$ comprises phenol, alkoxyphenyl, thioalkoxyphenyl, aryloxyphenyl, thioaryloxyphenyl, carboxyphenyl, thiocarboxyphenyl hydroxyphenol, and dihydroxyphenol, The compounds according to the present invention therefore include at least one phenol moiety (preferably at least two phenol moieties). As is further defined hereinbelow, each of the phenol moieties can be either unsubstituted or substituted, preferably by one or more hydroxy groups, thus being hydroxyphenol or dihydroxyphenol. Each of the phenol moieties can be present within the compounds of the present invention either per se, namely as a hydroxyphenyl moiety, or as an alkoxylated or carboxylated phenol moiety, namely, as an alkoxyphenyl or carboxyphenyl moiety, as is delineated hereinunder.

An "alkenyl" group refers to an alkyl group, as defined hereinabove, which consists of at least two carbon atoms and at least one carbon-carbon double bond.

An "alkynyl" group refers to an alkyl group, as defined hereinabove, which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A preferred example of a substituted aryl, according to the present invention is phenol.

As used herein, the term "phenol" refers to a phenyl substituted by a hydroxy group. The phenol group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A preferred example of a substituted phenol, according to the present invention, is hydroxyphenol.

As used herein, the term "hydroxyphenol", which also encompasses the term "dihydroxyphenol" refers to a phenol, as defined hereinabove, which is further substituted by one or more additional hydroxy groups. The additional hydroxy groups can be at the para, ortho and/or meta positions with respect to the hydroxy group of the phenol. The hydroxyphenol may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Other preferred examples of a substituted aryl, according to the present invention, include alkoxyphenyl, thioalkoxyphenyl, aryloxyphenyl and thioaryloxyphenyl.

As used herein, the term "alkoxyphenyl" refers to a phenyl substituted by an alkoxy group, as defined herein. A representative example of an alkoxy group is methoxy.

The term "thioalkoxyphenyl" refers to a phenyl substituted by a thioalkoxy group, as defined herein.

The term "aryloxyphenyl" refers to a phenyl substituted by an aryloxy group, as defined herein.

The term "thioaryloxyphenyl" refers to a phenyl substituted by a thioaryloxy group, as defined herein.

Each of the alkoxyphenyl, thioalkoxyphenyl, aryloxyphenyl and thioaryloxyphenyl groups may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Preferred substituents of the alkoxyphenyl, thioalkoxyphenyl, aryloxyphenyl and thioaryloxyphenyl groups include alkoxy, thioalkoxy, aryloxy and/or thioaryloxy groups, such that examples of preferred substituted alkoxyphenyl, thioalkoxyphenyl, aryloxyphenyl and thioaryloxyphenyl include dialkoxyphenyl, dithioalkoxyphenyl, diaryloxyphenyl and dithioaryloxyphenyl, and any other combination.

As used herein, the term "dialkoxyphenyl", refers to an alkoxyphenyl, as defined hereinabove, which is further substituted by one or more additional alkoxy groups. The additional alkoxy groups can be at the para, ortho and/or meta positions with respect to the alkoxy group of the alkoxyphenyl.

The term "dithioalkoxyphenyl", refers to a thioalkoxyphenyl, as defined hereinabove, which is further substituted by one or more additional thioalkoxy groups. The additional thioalkoxy groups can be at the para, ortho and/or meta positions with respect to the thioalkoxy group of the thioalkoxyphenyl.

The term "diaryloxyphenyl", refers to an aryloxyphenyl, as defined hereinabove, which is further substituted by one or more additional aryloxy groups. The additional aryloxy groups can be at the para, ortho and/or meta positions with respect to the aryloxy group of the aryloxyphenyl.

The term "dithioaryloxyphenyl", refers to a thioaryloxyphenyl, as defined hereinabove, which is further substituted by one or more additional thioaryloxy groups. The additional thioaryloxy groups can be at the para, ortho and/or meta positions with respect to the thioaryloxy group of the thioaryloxyphenyl.

Each of the dialkoxyphenyl, dithioalkoxyphenyl, diaryloxyphenyl and dithioaryloxyphenyl may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Other preferred examples of a substituted aryl, according to the present invention, include carboxyphenyl and thiocarboxyphenyl.

As used herein, the term "carboxyphenyl" refers to a phenyl substituted by an O-carboxy group, as defined herein. A representative example of an O-carboxy group is O-acetoxy.

The term "thiocarboxyphenyl" refers to a phenyl substituted by a thiocarboxy group, as defined herein.

The carboxyphenyl and the thiocarboxyphenyl may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

Preferred substituents include additional O-carboxy or thiocarboxy groups, such that examples of preferred substituted carboxyphenyl and thiocarboxyphenyl include dicarboxyphenyl and dithiocarboxyphenyl.

As used herein, the term "dicarboxyphenyl", refers to a carboxyphenyl, e.g., acetoxyphenyl, as defined hereinabove, which is further substituted by one or more additional carboxy groups. The additional carboxy groups can be at the para, ortho and/or meta positions with respect to the carboxy group of the carboxyphenyl.

The term "dithiocarboxyphenyl", refers to a thiocarboxyphenyl, as defined hereinabove, which is further substituted by one or more additional thiocarboxy groups. The additional thiocarboxy groups can be at the para, ortho and/or meta positions with respect to the thiocarboxy group of the thiocarboxyphenyl.

Each of the dicarboxyphenyl and dithiocarboxyphenyl may be additionally substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, phosphonyl, phosphinyl, phosphonium, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, and amino, as these terms are defined herein. Representative examples are piperidine, piperazine, tetrahydrofurane, tetrahydropyrane, morpholino and the like.

An "alkoxy" group refers to both an —O-alkyl and an —O-cycloalkyl group, as defined herein.

An "aryloxy" group refers to both an —O-aryl and an —O-heteroaryl group, as defined herein.

An "oxo" group refers to an =O group.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

An "O-carboxy" group refers to a R"C(=O)—O— group, where R" is as defined herein.

A "sulfinyl" group refers to an —S(=O)—R" group, where R" is as defined herein.

A "sulfonyl" group refers to an —S(=O)$_2$—R" group, where R" is as defined herein.

A "trihalomethyl" group refers to a —CX group wherein X is a halo group as defined herein.

A "trihalomethanesulfonyl" group refers to a X$_3$CS(=O)$_2$— group wherein X is a halo group as defined herein.

A "S-sulfonamido" group refers to a —S(=O)$_2$—NR'R" group, with R' and R" as defined herein.

A "N-sulfonamido" group refers to n R'S(=O)$_2$—NR" group, where R' and R" are as defined herein.

A "trihalomethanesulfonamido" group refers to an X$_3$CS(=O)$_2$NR'— group, where R' and X are as defined herein.

An "O-carbamyl" group refers to an —OC(=O)—NR'R" group, where R' and R" are as defined herein.

An "N-carbamyl" group refers to an R"OC(=O)—NR'— group, where R' and R" are as defined herein.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —NR'R" group where R' and R" are as defined herein.

A "C-amido" group refers to a —C(=O)—NR'R" group, where R' and R" are as defined herein.

An "N-amido" group refers to an R'C(=O)—NR" group, where R' and R" are as defined herein.

An "urea" group refers to an —NR'C(=O)—NR"R'" group, where R' and R" are as defined herein and R'" is defined as either R' or R".

A "guanidino" group refers to an —R'NC(=N)—NR"R'" group, where R', R" and R'" are as defined herein.

A "guanyl" group refers to an R'R"NC(=N)— group, where R' and R" are as defined herein.

An "azo" group refers to a —N=N group.

The term "phosphonyl" describes a —O—P(=O)(OR')(OR") group, with R' and R" as defined hereinabove.

The term "phosphinyl" describes a —PR'R" group, with R' and R" as defined hereinabove.

Preferred phenol-containing compounds according to the present invention therefore include, for example, phenol red and analogs thereof, such that in the Formula above X is carbon; Y is oxygen; Z is carbon or sulfur; and at least one of R$_5$ and R$_6$ is oxo, as this term is defined hereinabove. Such compounds include a heteroalicyclic ring, fused with phenyl, and further substituted by one or more phenol or phenyl groups, such that at least one of R$_5$-R$_{10}$ is phenol or hydroxyphenol, as defined hereinabove. Such compounds in which at least one, and preferably two, of R$_5$-R$_{10}$ are hydroxyphenol include, for example, pyrocatechol violet and analogs thereof.

Compounds in this category, in which Z is sulfur, are typically phenol red analogs, whereas compounds in which Z is carbon are typically phenolphthaleine analogs.

Even more preferred compounds according to the present invention, include compounds having the Formula above, in which X is carbon; Y is R$_{13}$R$_{14}$C—CR$_{15}$R$_{16}$; and Z is oxygen. Such compounds therefore include a tetrahydropyrane ring fused to phenyl.

Preferred examples of compounds in this category include analogs and derivatives of catechins such as, for example, analogs and derivatives of epicatechin, epigallocatechin, epigallocatechin gallate and the like, all include two hydroxy group at the R$_1$ and R$_3$ positions and a hydroxyphenol or dihydroxyphenol group, directly or indirectly attached to the tetrahydropyrane ring, at one or more of the R$_{13}$-R$_{16}$ positions in the Formula above.

Additional preferred examples of these compounds include an oxidized tetrahydropyrane ring fused to a phenyl, such that R$_9$ is oxo; and R$_{10}$ is absent.

Further additional preferred compounds in this category include tocopherol and analogs thereof, which include one or more alkyl groups at the R$_{13}$-R$_{16}$ positions, whereby the alkyl groups can include lower alkyls (e.g., methyl) and/or alkyls having more than 8 carbon atoms.

Further according to the present invention, each of the compounds described above can further be in a dimeric form. Such a dimeric form includes two moieties having the Formula above, attached therebetween via R$_1$-R$_{16}$, directly or indirectly.

Examples of phenol-containing compounds which can be used in accordance with the present invention therefore include, but are not limited to, phenol red, pyrocatechol violet, phenolphthaleine, catechin, epigallocatechin gallate, epicatechin gallate, epicatechin, epigallocatechin, eriodictyol, quercetin, procyanidin, hydroxyphenyl, tocopherol, bromophenol red, analogs thereof, derivatives thereof and any combination thereof.

The presently most preferred phenol-containing compounds according to the present invention are phenol red, pyrocatechol violet and compounds of the catechin gallate family.

However, additional preferred compounds which can be used in accordance with the present invention include the mono-, di-, tri- and tetra-alkoxy (e.g., methoxy) or carboxy (e.g., acetoxy) derivatives of the compounds listed above. Such derivatives are meant to include compounds in which one or more of the hydroxy groups in the phenol or hydroxyphenol moieties are derivatized by, e.g., an alkyl or acyl group, resulting in an alkoxyphenyl moiety, a dialkoxyphenyl moiety, a carboxyphenyl moiety or a di-carboxyphenyl moiety.

Such a derivatization of the hydroxy groups, which results in the replacement of one or more of the phenol moieties by an alkoxyphenyl moiety, a dialkoxyphenyl moiety, a carboxyphenyl moiety or a di-carboxyphenyl moiety, as well as analogs thereof (e.g., aryloxyphenyl, thioalkoxyphenyl, and the like, as is detailed hereinabove) is highly advantageous since it reduces the hydrophilic nature of the compounds and thus enhances their absorption in the intestines.

As is well known in the art, hydrophilic compounds are typically characterized by relatively low absorption due to poor permeability across human intestinal epithelial. Due to these low absorption parameters, treatment with hydrophilic compounds requires the administration of high doses, when administered orally. Hence, reducing the hydrophilic nature of the compounds described above provides for enhanced absorption thereof, particularly in the intestines, and enables an effective oral administration thereof. The effect of reducing the hydrophilic nature of compounds on their absorption was clearly shown in several models, including the Caco-2 cells and parallel artificial membrane permeation assay (PAMPA). These studies demonstrated that increased hydrophobicity significantly improves the permeability of small organic compounds [Ano (2004) Bioorg Med Chem. 12:257-264; Ano (2004) 12: 249-255].

Representative examples of such derivatives include, but are not limited to, methoxy phenol red and acetoxy phenol red, in which one phenol moiety in phenol red is replaced by a methoxyphenyl or an acetoxyphenyl moiety, respectively, and dimethoxy phenol red and diacetoxy phenol red, in which the two phenol moieties in phenol red are replaced by two methoxyphenyl or acetoxyphenyl moieties, respectively.

Of a particular importance are the mono derivatives of phenol red, namely, methoxy phenol red and acetoxy phenol red and analogs thereof. These mono derivatives simultaneously provide for (i) enhanced inhibition activity due to the presence of hydroxy groups; (ii) enhanced oral bioavailability due a partial hydrophilic nature thereof; and (iii) enhanced absorption due to a partial hydrophobic nature thereof, as is detailed hereinabove.

Hence, the phenol red mono derivatives of the present invention, by combining enhanced inhibition activity, enhanced oral bioavailability and enhanced absorption, are highly advantageous.

Another group of compounds which can be used in accordance with the present invention are indole-derivatives (see for example, U.S. Provisional Patent Application No. 60/649, 574), such as having the general formula:

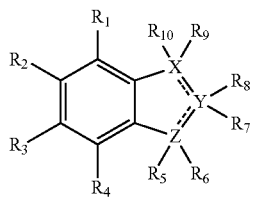

Formula II a pharmaceutically acceptable salt thereof, or a prodrug thereof,
wherein:
the dashed line denotes a double bond either between X and Y, or, between Y and Z;
X, Y and Z are each independently selected from the group consisting of carbon and nitrogen, whereas at least one of X, Y, and Z is nitrogen; and
$R_1$-$R_{10}$ are each independently selected from the group consisting of hydrogen, lone pair electrons, hydroxy, alkyl, cycloalkyl, phenyl, phenol, hydroxyphenol, dihydroxyphenol, aryl, alkenyl, alkynyl, heteroaryl, heteroalicyclic, halo, alkoxy, aryloxy, thiohydroxy, thioalkoxy, thioaryloxy, C-carboxy, O-carboxy, thiocarboxy, carbonyl, oxo, thiocarbonyl, sulfinyl, and sulfonyl, or absent, or, alternatively, at least two of $R_1$-$R_{10}$ form at least one five- or six-membered aromatic, heteroaromatic, alicyclic or heteroalicyclic ring.

Thus, preferred indole-derived compounds which conform to the above illustratively described general formula, and which can be used for use in accordance with the present invention, are therefore indole derivatives, being compounds having an aromatic ring fused to a heterocyclic ring having at least one nitrogen atom. The parent compound, indole, is a heteroaromatic compound having a phenyl ring fused to a pyrrole ring and thus comprises a completely conjugated pi-electron system.

However, an indole derivative, according to the present invention, encompasses any aromatic moiety that is fused to a heterocyclic ring containing one or more nitrogen atoms (for example, one, two or three nitrogen atoms). Depending of the location of the pi-electrons of the double bond (between X and Y or Y and Z, see, the formula above) and the nature of the ring atoms (carbon and/or nitrogen), the electronic structure of an indole derivative according to the present invention can include either a partially or completely conjugated pi-electron system.

Thus, an indole derivative, according to the present invention, encompasses, for example, substituted or unsubstituted indoles, substituted or unsubstituted purines, substituted or unsubstituted carbazoles and substituted or unsubstituted phenyl ring fused to a substituted or unsubstituted imidazole, pyrazole, thiazine, and the like, with substituted or unsubstituted indoles being the presently preferred indole derivatives.

Thus, preferred compounds which can be used for use in accordance with the present invention, are compounds which have the above illustratively described general formula, wherein each of X and Y is carbon, and Z is nitrogen, whereby the double bond (dashed line) is preferably between X and Y.

Further preferred compounds for use in accordance with the present invention, are compounds which have the above illustratively described general formula, wherein one or more of $R_1$-$R_{10}$ comprises a hydroxy group. In such compounds, the one or more hydroxy groups are directly or indirectly attached to the indole derivative skeleton, such that at least one of $R_1$-$R_{10}$ is either hydroxy or, for example, a hydroxyalkyl, as defined hereinabove.

Particularly preferred compounds which can be used for use in accordance with the present invention, are indoles substituted by a hydroxy group and are therefore compounds which have the above illustratively described general formula, wherein each of X and Y is carbon, and Z is nitrogen, the double bond (dashed line) is between X and Y, and at least one of $R_1$-$R_{10}$ is a hydroxy group. Preferably, in such hydroxy group containing compounds, at least one of $R_1$, $R_3$, $R_4$, and $R_9$ is a hydroxy group, and more preferably, $R_1$ or $R_9$ is a hydroxy group. More preferably, in such hydroxy group containing compounds, each of $R_2$-$R_5$ and $R_7$ is hydrogen and $R_6$, $R_8$ and $R_{10}$ are absent.

A representative example of such a hydroxy containing compound is 3-hydroxyindole, such that in the general formula, $R_1$ is hydrogen and $R_9$ is the hydroxy group. Another representative example of such a hydroxy containing compound is 4-hydroxyindole, such that in the general formula, $R_1$ is the hydroxy group and $R_9$ is hydrogen.

Additional particularly preferred compounds which can be used for use in accordance with the present invention, are indoles substituted by one or more hydroxyalkyl groups and are therefore compounds which have the above illustratively described general formula, wherein each of X and Y is carbon, and Z is nitrogen, the double bond (dashed line) is between X and Y, and at least one of $R_1$-$R_{10}$ is a hydroxyalkyl. Preferably, in such hydroxyalkyl containing compounds, at least one of $R_7$ and $R_9$ is a hydroxyalkyl. More preferably, in such hydroxyalkyl containing compounds, each of $R_1$-$R_5$ is hydrogen, and $R_6$, $R_8$ and $R_{10}$ are absent. More preferably, in such hydroxyalkyl containing compounds, at least one of $R_7$ and $R_9$ is a hydroxymethyl type of hydroxyalkyl.

A representative example of such a hydroxyalkyl containing compound is indole-3-carbinol (3-hydroxymethyl indole), such that in the general formula, $R_7$ is hydrogen and $R_9$ is a hydroxymethyl.

Examples of other non-protein anti-amyloid agents which can be used in accordance with the present invention include, but are not limited to, nicotine [Salomon (1996) Biochemistry 35:13568-13578], acridine and acridine orange, Congo red, methylene blue, tetracycline and Thioflavin-T [each of which described by Aitken (2003) Biochem. J. 374:779-784] and non-steroidal anti-inflammatory drugs as listed in Table 2 below.

TABLE 2

NSAIDs—nonsteroidal anti-inflammatory drugs

| DRUG | BRAND NAME(S) |
|---|---|
| Traditional NSAIDs | |
| Diclofenac potassium | Cataflam |
| Diclofenac sodium | Voltaren, Voltaren XR |
| Diclofenac sodium with misoprostol | Arthrotec |
| Diflunisal | Dolobid |
| Etodolac | Lodine, Lodine XL |
| Fenoprofen calcium | Nalfon |
| Flurbiprofen | Ansaid |
| Ibuprofen | Motrin, Advil, Motrin IB, Nuprin |
| Indomethacin | Indocin Indocin SR |
| Ketoprofen | Orudis Oruvail Actron, Orudis, KT |
| Meclofenamate sodium | Meclomen |
| Mefenamic acid | Ponstel |
| Meloxicam | Mobic |
| Nabumetone | Relafen |
| Naproxen | Naprosyn, Naprelan |
| Naproxen sodium | Anaprox, Aleve |
| Oxaprozin | Daypro |
| Piroxicam | Feldene |
| Sulindac | Clinoril |
| Tolmetin sodium | Tolectin |
| COX-2 Inhibitors | |
| Celecoxib | Celebrex |
| Rofecoxib | Vioxx |
| Valdecoxib | Bextra |
| Salicylates | |
| Acetylated Salicylates | |
| Aspirin | Anacin, Ascriptin, Bayer, Bufferin, Ecotrin, Excedrin tablets |
| Nonacetylated Salicylates | |
| Choline and magnesium salicylates | CMT, Tricosal, Trilisate |
| Choline salicylate (liquid only) | Arthropan |
| Magnesium salicylate | Magan, Mobidin, Mobogesic, Arthritab, Bayer Select, Doan's Pill |
| Salsalate | Amigesic, Anaflex 750, Disalcid, Marthritic, Mono-Gesic, Salflex, Salsitab |
| Sodium salicylate (Available as generic only) | |

Accordingly, the anti-amyloid agents of the present invention (also referred to as compounds of the present invention, described hereinabove) can be provided to the subject per se, or as part of a pharmaceutical composition where it is mixed with a pharmaceutically acceptable carrier.

As used herein a 'pharmaceutical composition' refers to a preparation of one or more of the active ingredients described herein with other chemical components such as physiologically suitable carriers and excipients. The purpose of a pharmaceutical composition is to facilitate administration of a compound to the subject treated.

Herein the term 'active ingredient' refers to the compound, which is accountable for the biological effect.

Hereinafter, the phrases 'physiologically acceptable carrier' and 'pharmaceutically acceptable carrier' which may be interchangeably used refer to a carrier or a diluent that does not cause significant irritation to the subject and does not abrogate the biological activity and properties of the administered compound. Preferred carriers of the pharmaceutical composition of the present invention include, but are not limited to, polyethylene glycol (PEG), a biocompatible polymer with a wide range of solubility in both organic and aqueous media (Mutter et al. (1979).

Herein the term 'excipient' refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in 'Remington's Pharmaceutical Sciences,' Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

According to another aspect of the present invention, there is provided an article-of-manufacture including a packaging material and a pharmaceutical composition identified for treating amyloid associated diseases being contained within the packaging material, the pharmaceutical composition including, as an active ingredient, the compound described hereinabove, and a pharmaceutically acceptable carrier.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the use of other PKU drugs (e.g., tetrahydrobiopterin) and diets (phenylalanine poor nutrition) can be used in combination with the agents of the present invention to increase therapeutic efficacy thereof.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Methods Summary

Material—Amino acids were purchase from Sigma. Fresh stock solutions were prepared by dissolving the amino acid at $ddH_2O$, PBS or Dulbecco's Modified Eagle Medium (DMEM) (Beit Haemek, Israel) at various concentrations ranging from 6 µM to 120 mM.

Transmission electron microscopy—Phenylalanine was dissolved in ddH2O to concentration of 6 mM. Then a 10 µl aliquot of this solution was placed on 400 mesh copper grids. After 1 minute, excess fluids were removed. For negative staining, the grid was stained with 2% uranyl acetate in water and after two minutes excess fluids were removed from the grid. Samples were viewed using a JEOL 1200EX electron microscope operating at 80 kV.

Scanning electron microscopy—Phenylalanine was dissolved in ddH2O or 10% human serum to concentration of 6 mM or 12 mM respectively. Then a 10 µl aliquot of the solution was placed on microscope glass cover slip and coated with gold. Scanning electron microscopy images were made using a JSM JEOL 6300 SEM operating at 5 kV.

Environmental scanning electron microscopy—Phenylalanine was dissolved in dd H2O to concentration of 6 mM. A 10 µl aliquot of the solution was placed on a metal stand. Environmental scanning electron microscopy images were made using Quanta 200 FEG Field Emission Gun ESEM operating at 10 kV.

Congo red staining and birefringence—Phenylalanine was dissolved in ddH2O to concentration of 6 mM. Then a 10 µl aliquot of the solution was allowed to dry on a glass microscope slide. Staining was performed by the addition of 10 µl solution of 80% ethanol saturated with Congo red and NaCl. Birefringence was determined with a SZX-12 Stereoscope (Olympus, Hamburg, Germany) equipped with a polarizing stage.

ThT staining and confocal laser microscopy imaging—10 µl ThT solution (2 mM, PBS buffer) were mixed with 10 µl phenylalanine fibril (6 mM, ddH2O). An LSM 510 confocal laser scanning microscope (Carl Zeiss Jena, Germany) was used at excitation and emission wavelengths of 458 and 485 nm, respectively.

Electron diffraction—Phenylalanine was dissolved in ddH2O to concentration of 6 mM. Then a 10 µl aliquot of this solution was placed on 400 mesh copper grids. After 1 minute, excess fluid was removed. Electron diffraction experiments were performed on an FEI Tecnai F20 microscope FEI at 200 kV with a field-emission gun, and samples cooled to liquid nitrogen temperatures using a Gatan 626 cryoholder. Low dose methods were used with total dose to the sample of ~50 electrons per Å2. Electron diffraction patterns were recorded directly to the CCD camera (TVIPS F415).

NMR—NMR spectra were recorded on a AC 200 MHz, Bruker spectrometer, using Bruker Topspin 2.1 software. The chemical shifts were expressed in δ relative to TMS ($\delta=0$ ppm). The spectra were recorded in $D_2O$ as a solvent, at room temp. 1H-NMR ($D_2O$-d6): $\delta=2.9$-3.3 (m, CH2), 3.8-3.9 (m, CH), 7.1-7.3 (m, 5H aromatic).

HPLC—Reverse phase HPLC showed >97% purity. Dionex HPLC system with Ultimate 3000 pump, Ultimate 3000 autosampler and Ultimate 3000 variable multiwave detector, controlled via Chromeleon chromatography workstation. Column: LiCroCART Purospher STAR RP 4.6 mm, 5 µm C18e, Buffer A: 0.1% TFA in water, Buffer B: 0.1% TFA in acetonitrile, Flow: 1 ml/min, Binary Gradient: t=0-5; % A=100%, t=5-20; % B=0%-100%, t=20-25, % B=100%, 260 nm, Diluent 100% A, TFA (Sigma) ≥99.0% (GC), for HPLC, Acetonitrile (Bio-Lab) HPLC grade, Water (Bio-Lab) HPLC grade.

Phenylalanine concentration at equilibrium—Phenylalanine was dissolved in water to a concentration of 1 mg/ml, the solution absorbance was measured at 256 nm. Then the assemblies were centrifuged in Optima TLX1 Benchtop Ultracentrifuge for 1 hour at 4° C. The supernatant absorbance was measured at 256 nm.

Cell cytotoxicity experiments—CHO cells (2×105 cells/mL) were cultured in 96-well micro plates (100 µL/well) and incubated overnight at 37° C. 100 µL of phenylalanine was added to each well dissolved in Dulbecco's Modified Eagle Medium (DMEM) (Beit Haemek, Israel) at various concentrations. Each experiment was repeated 3 times. Following incubation for 6 hours at 37° C., cell viability was evaluated using the 3-(4,5-dimethylthiazolyl-2)-2,5-diphenyltetrazolium bromide (MTT) assay. Briefly, 20 µL of 5 mg/mL MTT dissolved in PBS was added to each well. After 4 hours incubation at 37° C., 100 µL of extraction buffer [20% SDS dissolved in a solution of 50% dimethylformamide and 50% DDW (pH 4.7)] was added to each well, and the plates were incubated again overnight at 37° C. Finally, color intensity was measured using an ELISA reader at 570 nm.

Scanning electron microscopy imaging of CHO cells—CHO cell were cultured on glass cover slips located in 24-well micro plates, then incubated with various concentration of phenylalanine fibrils for 6 hour at 37° C., as described in the cell cytotoxicity experiments section. The cell were fixated on the glass cover slip with 2.5% glutaraldehyde, then dehydrated and coated with gold. Scanning electron microscopy images were made using a JSM JEOL 840A SEM operating at 5 kV.

Antibody formation—Phenylalanine was dissolved in ddH2O at concentration of 120 mM to form fibrils; the rabbits were immunized five times subcutaneous at 14-day intervals with Freund's adjuvants. Seven days after each injection, the mice were bled and their serum tested using slot-blot analysis.

Rabbits Antibodies' Immuno-testing using transmission electron microscopy analysis—The immunolabeling was visualized by 18 nm gold conjugated goat anti-mouse antibodies (Electron Microscopy Sciences, Washington, USA). Phenylalanine was adhered to copper grid as described in the transmission electron microscopy section. Then, the grid was blocked with 1% BSA/3% goat serum for 30 minutes. Sample were incubated with the serum diluted 1:200 in TBS/1% milk for 30 minutes, washed five times with 0.1 BSA/TBS, then incubated with the secondary antibody for 30 minutes and washed. Samples were viewed using a JEOL 1200EX electron microscope operating at 80 kV.

Rabbits Antibodies' Immuno-testing using slot-blot analysis—100 µl solution of phenylalanine fibrils (15, 30, 60 and 120 mM) applied via a vacuum manifold onto a nitrocellulose filter using a slot-blot apparatus. After blocking the membrane with 1% milk in TBS for 1 hour at room temperature, the membrane was washed briefly with TBS and incubated with the serum diluted 1:5000 in TBS/2% milk for 1 hour at room temperature. Then, the membrane was washed briefly with TBS and incubated with HRP-conjugated goat anti rabbit antibodies. The membrane was developed using ECL reagents (NEN, USA) according to the supplier's instructions. For the control experiment BSA protein was applied on the nitrocellulose filter instead of the phenylalanine fibrils.

Dot blot analysis of pahenu2 mice—Proteins or samples in a total volume of 100 µl ddH2O or PBS were applied via a vacuum manifold onto a PVDF membrane filter using a dot-blot apparatus (Schleicher and Schuell, USA). After blocking the membranes with 3% (v/v) non-fat milk in PBS for overnight at 4° C., the membrane was washed briefly with PBS followed by incubation with mouse (pahenu2 homozygous, pahenu2 heterozygous and wild-type plasma or specific anti-Phe fibrils rabbit serum for 1 h at room temperature. The signal was detected using the appropriate anti-mouse and anti-rabbit HRP-conjugated secondary antibodies (Jackson Laboratories, West Grove, Pa.). After three washes with PBS the PVDF filter membranes were developed with the ECL reagent (Pierce, USA). The protein blot was visualized using X-ray film.

Immuno precipitation and cell cytotoxicity experiments—Phenylalanine solution at concentration of 7.5, 1.87, 0.46, 0.11 were either incubated with CHO cell or immuno-precipitate and then the solutions, without the fibrils, were incubated with CHO cell according to cell cytotoxicity experiments detailed above. Samples were immuno-precipitated with anti-phenylalanine fibrils antibodies (1:10) over night at 4° C. (previously purified on protein A column, in PBS+2% BSA).

Congo red staining of brain tissue of pahenu2 mice—15 µm coronal brain sections of pahenu2 homozygous and heterozygous mice were prepared using cryostat. Brain samples were fixed in 70% ethanol for 1 min, washed in DDW for 2 min and stained with previously filtered Congo red solution for 10 min. Following the staining, the samples were washed in DDW for 2 min and washed 8-10 times in NaOH-ethanol solution (0.5 ml 1% NaOH+49.5 ml 50% ethanol) till the red color disappears. Finally, the samples were washed in DDW and the signal was detected using fluorescent microscope (absorption at 498 nm, emission at 614 nm).

Immunohistological staining of mouse brain tissue—Brain samples were fixed in 4% paraformaldehyde (PFA) (in PBS) for 5 min and washed for 5 min in DDW. Brain slices were blocked with 2% BSA solution (in PBS) for 20 min, then washed 3 times in DDW and incubated with specific anti-Phe fibrils rabbit antibodies solution, dilution 1:20, (previously purified on protein A column) (in PBS+2% BSA) for 1 hour at room temperature. Following the incubation, the samples were washed 3 times in DDW and incubated with goat-anti-rabbit-F488 conjugated secondary antibody. Signal was detected by fluorescent microscope (absorption at 495 nm, emission at 519 nm).

Immunohistological staining of human brain tissue: Brain samples, acquired from the London Neurodegenerative Diseases Brain Bank, were fixed in paraffin. Consecutive sections were de-paraffinized, with xylene, fixed in 4% paraformaldehyde and treated with 0.3% $H_2O_2$ (in PBS). Sections were then heated in citric acid pH=6 for 5 minutes, and were treated with 0.25% Triton X-100 for 3 minutes. The sections were blocked using 2% BSA solution (in PBS) for 20 min, then washed 3 times in PBS and incubated with specific rabbit-anti-Phe fibrils antibodies solution, dilution 1:50, (previously purified on protein A column, in PBS+2% BSA) for 1 hour at room temperature, along with pre-immuned rabbit serum as control. Following the incubation, the samples were washed 3 times in PBS and incubated with biotinilated goat-anti-rabbit conjugated secondary antibody (Vector laboratories, BA-1000) diluted 1:250 for 1 hour at room temperature and washed with PBS. Sections were then treated with ABC reagent (Vector laboratories, vectastatin ABC kit, PK-6100), and developed with diaminobenzidine and hydrogen peroxide (vector laboratories, SK-4100). Signal was detected by light microscope.

Results and Discussion

At a millimolar concentration range of phenylalanine, transmission electron microscopy (TEM) analysis indicated the occurrence of well-ordered and elongated assemblies (FIG. 1A). Scanning electron microscopy (SEM) was also used to study the three dimensional structures of the fibrils (FIG. 1B) as well as environmental SEM (ESEM) to study fibrillar structures in humid environment (FIG. 1C). Both SEM and ESEM micrographs showed areas covered with discrete assemblies which demonstrate that the assemblies are relatively homogeneous and evidently are discrete entities with persistence length in the order of few micrometers. Also it was demonstrated, by SEM analysis that phenylalanine fibrillar structures form in human serum a more physiological relevant environment (FIG. 1D). Both HPLC and NMR analysis clearly indicated that no covalent bonds between the phenylalanine monomers were formed, and the highly ordered fibrils are supramolecular assemblies (FIGS. 1J-K). All these data show that phenylalanine assembles into amyloid like structures and that this assembly can take place under physiologically relevant conditions.

Another characteristic of amyloid fibrils is the presence of typical yellow-green birefringence upon staining with Congo red (CR) and microscopic examination under cross-polarization. This results from the high order of the assemblies at the molecular-level. Thus we examined these assemblies using CR staining in order to gain further information on their internal order. Upon microscopic examination, a characteristic birefringence was observed similar to that of amyloid fibrils (FIG. 1E). Another common method for quantitative assessment of amyloid fibrils is the Thioflavin T (ThT) fluorescence assay which reflects the change in fluorescence of the dye upon its interaction with the ordered assemblies. The ThT characteristic was used to visualize the phenylalanine fibrils and an excitation shift typical to amyloid fibrils binding was observed. Fluorescence confocal microscopy analysis of the fibrils, dyed with ThT, showed the presence of elongated ordered structures (FIG. 1F).

An additional method to confirm the degree of order of fibrillar structures is the use of electron diffraction. This was previously elegantly used to probe the ultra-structure of amyloid fibrils (15, 23). Indeed, also in the case of the phenylalanine fibril, electron diffraction studies gave a strong indication to the high organization of the assemblies. An electron diffraction pattern of a single fibril was consistent with a unit cell of a=11.63±0.27 Å, c=4.6±0.06 Å (for n=5 measurements), where a is oriented normal to the long axis of the crystal, and c along the fiber axis (FIG. 1G).

Molecular dynamics simulations with a generalized-Born implicit solvent model were carried out to shed light on the structures of the early aggregates of phenylalanine. Multiple microsecond-long simulations were started from 27 mono-dispersed phenylalanine molecules at different values of pH and in the presence or absence of counterions. Four different values of the concentration of phenylalanine were used (1, 6, 30, and 100 mM) and three temperature values (280, 300, and 310 K). Ordered aggregation was observed at some but not all conditions. At high pH (i.e., neutral amino group and negatively charged carboxy group) in the presence of counterions, filamentous aggregates were observed at high concentration and all values of the temperature (FIG. 1H). Analysis of the ensemble of self-assembled structures yields a distribution of interatomic distances with two peaks at about 5 and 11 Angstroems (FIG. 1I) which correspond to the distances between neighboring phenylalanines and the laminal spacing, respectively (FIG. 1H). Pairs of neighboring phenylalanines are involved in direct hydrogen bonds or salt-bridged polar interactions. Notably, the distribution of distances is in agreement with the aforementioned electron diffraction pattern.

These findings confirm that phenylalanine fibrillar assemblies have a high degree of structural order and are not the product of irregular aggregation. In that sense, they possess characteristics similar to those of amyloid fibrillar deposits. It may be concluded that the fibrils formed by phenylalanine closely resemble amyloid structures by all the physical assays used.

Figure 2A:
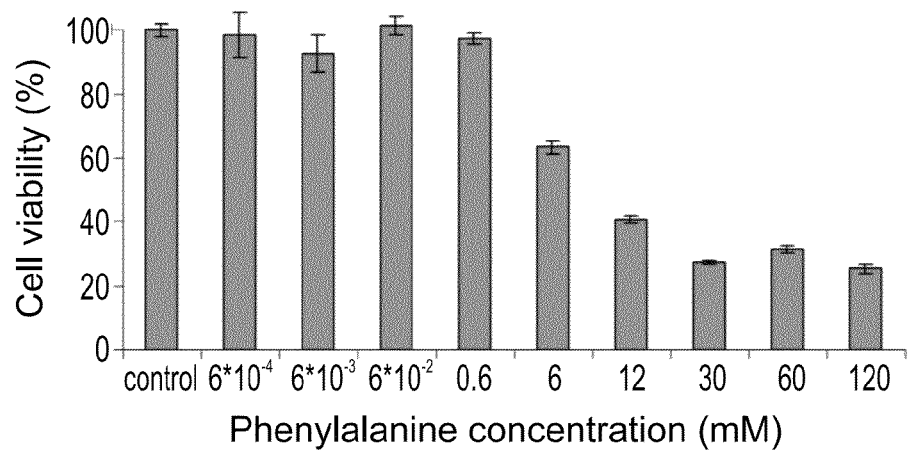
Figure 2B:
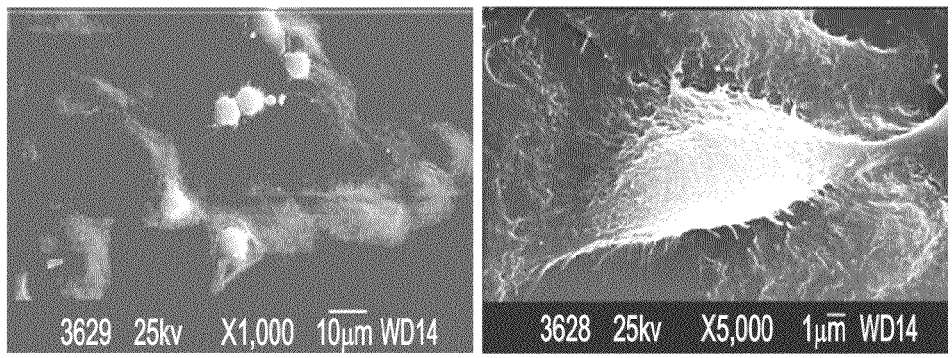
Figure 2C:
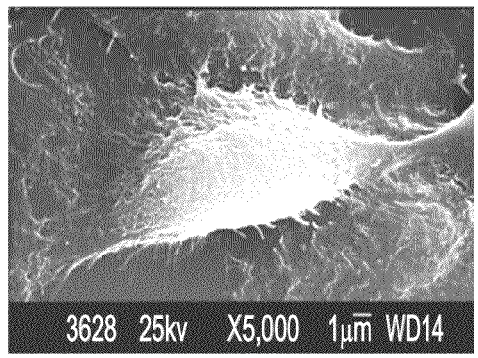
Figure 2D:
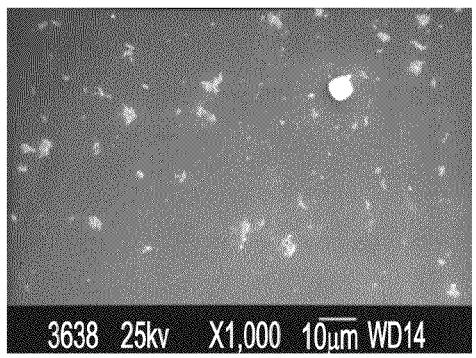
Figure 2E:
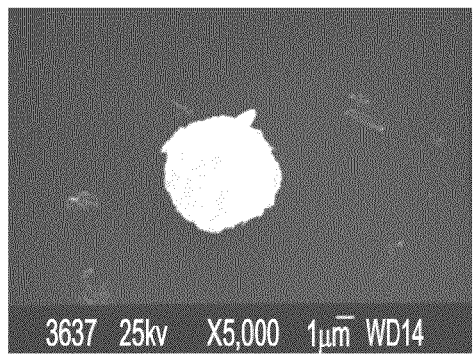
Figure 2F:
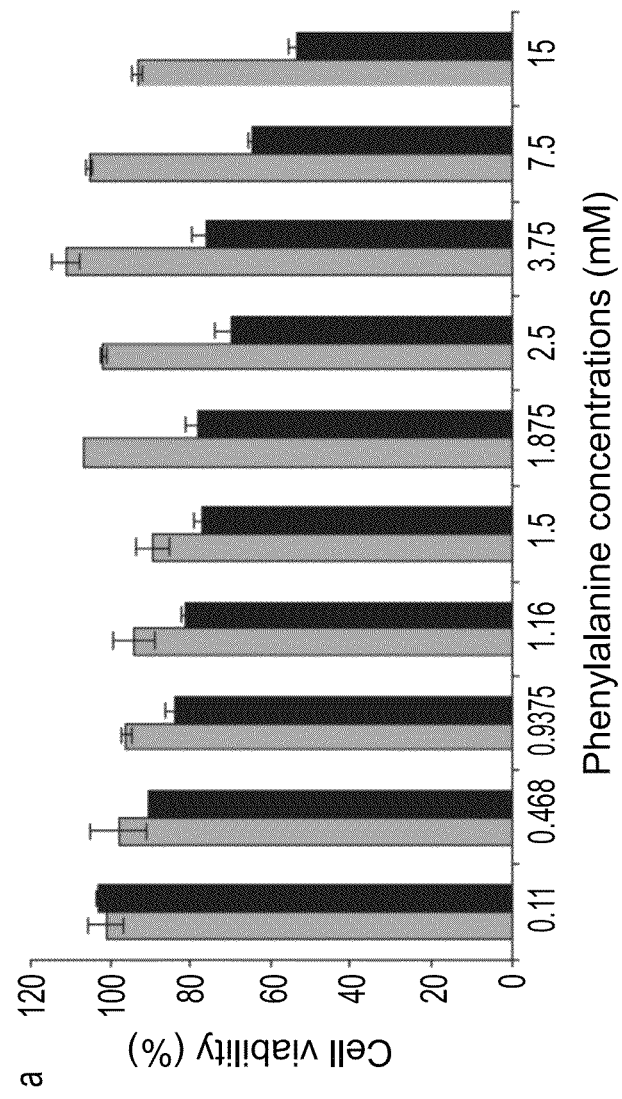

The present inventors next examined whether, like many amyloid structures, phenylalanine assemblies have a cyto-toxic effect. This was examined in a physiological range of concentration, similar to that detected in untreated PKU patients. We performed in vitro cellular viability experiments. To this end, elevated concentrations of phenylalanine ranging from 0.1 µM to 15 mM were added to cultured PC12 cell line were added to cultured PC12 cells. The phenylalanine fibrils exhibited a toxic effect on PC12 cell culture using the MTT assay (FIG. 2F). In the presence of 1.8 mM phenylalanine, PC12 cell viability was decreased to approximately 80%. Moreover, in the presence of phenylalanine at a concentration of 7.5 mM the cells viability was approximately 65% (FIG. 2F), suggesting a dose-dependent response. In the presence of 6 mM phenylalanine, CHO cell viability was decreased to 84%. Moreover, the viability of the cells in the presence of phenylalanine at concentration of 12 mM was lower than 40% (FIG. 2A). The present assay is performed at much shorter time scales than those of disease progression and this may account for the slightly elevated concentrations than those typically found at PKU patients. It is also possible that such high concentrations of phenylalanine occur pathologically in PKU patients due to transient local high concentration in the brain. Alanine, an average-sized amino acid that does not form fibrillar structures at examined concentrations, was used as a negative control in cytotoxicity and, as expected, did not demonstrate a toxic effect. The present inventors further assessed the influence of the phenylalanine fibrils on the CHO cells using scanning electron microscope. Changes were observed in the CHO cell morphology followed by incubation with phenylalanine fibrils. In the absence of phenylalanine fibrils the cells had an elongated shape (FIGS. 2, B and C) whereas the phenylalanine treated cells seemed smaller and rounded (FIGS. 2, D and E). A very low density of the phenylalanine-treated cells was observed as compared to the untreated cells. Based on these results, it may be suggested that phenylalanine pathology in PKU patients is due to the toxic effects of fibril formation at millimolar concentration.

One of the key prospects for amyloid disease treatment is the use of antibodies that specifically recognize and clear fibrillar assemblies and not the corresponding monomeric species. In order to examine whether the phenylalanine fibrils represent a unique immunological entity, the present inventors tried to produce specific antibodies against the phenylalanine fibrils. Rabbits were immunized with the fibrils, and their serum was tested for specificity to the assemblies. An immuno-gold assay was used in order to show the antibodies affinity to the fibrils; the fibrils were specifically marked with gold labeled secondary antibodies mediated by the serum antibodies, as can be observed in the TEM images (FIG. 3A).

While control analysis of phenylalanine fibrils, marked only with gold labeled, secondary antibodies, did not show any specificity to the fibrils (FIG. 4). In addition, a slot-blot analysis was performed for quantitative assessment of the serum antibodies affinity to the fibrils, in which the antibodies exhibited higher affinity to elevated fibrils concentrations (FIG. 5). Moreover, the specificity of the antibodies was demonstrated, as no cross-reactivity was found when the antibodies were incubated with the Parkinson's α-synuclein amyloid deposits or diphenylalanine peptide nanotubes[13] (FIGS. 6A-B). In addition low binding was observed using the control pre-immune serum (FIG. 5). This provides a clear indication for the formation of distinctive immunological epitope as observed in amyloid disorders.

Furthermore, the anti-Phe fibril antibodies were used for immunoprecipitation (IP) of the phenylalanine assemblies from the solution and to assess the assemblies' contribution to the toxic effect on cell culture. FIG. 3B compares the cytotoxic effect of phenylalanine assemblies prior and following the IP. Phenylalanine assemblies at concentration of 1.87 mM and 7.5 mM exhibited only 56% and 44% cell viability respectively; however, after IP the cell incubated with the solutions exhibited elevation in their viability to 72% and 107% cell viability, respectively, as measured by the MTT assay. The resemblance between these structures and amyloid assemblies, and the ability to raise antibodies against the phenylalanine fibrils further implies for the possibility for an imminent immunological treatment for PKU. Similar immunological approaches are being currently explored for Alzheimer's disease. The prospects of such treatment for PKU patients could drastically improve their quality of life.

To prove that these assemblies exist in vivo we examined sera samples obtained from a genetic mouse model of PKU (pah$^{enu2}$), deficient in phenylalanine hydroxylase activity (26). The present inventors were interested in analyzing the presence of anti-Phe fibril antibodies that will indicate on the presence of Phe fibril in the PKU mouse model. Using the dot blot assay anti-Phe fibril antibodies specifically in pah$^{enu2}$ homozygous mice serum were observed (FIG. 3C). Moreover, anti-Phe antibodies were not detected in control pah$^{enu2}$ heterozygous mice serum and in normal mouse serum (FIG. 3C). The presence of phenylalanine fibrils in brain tissue of pah$^{enu2}$ mice was further studied. Histology staining experiments were performed using Congo red and anti-Phe fibrils immunohistology staining techniques. According to staining results, there is an evidence for the presence of amyloid-like plaques in pah$^{enu2}$ mice (FIG. 3, D to I). The plaques were detected especially in the hippocampus (FIGS. 3, D to F) and close to blood vessels (FIGS. 3, G to I). Interestingly, significant necrosis and edema in the dentate gyrus was mentioned as well, in previous studies on phenylketonuria (27). In addition, the co-localization of Congo red and anti-Phe antibodies staining provides evidence that the plaques consist of amyloid-like phenylalanine fibrils. DAPI staining, a non-specific staining of double-stranded DNA, of plaque sections detected glia cell infiltration to the region. In addition, all control histological staining showed no evidence of phenylalanine assemblies: homozygous pah$^{enu2}$ mice brain tissue, stained with antibodies derived from pre-immune serum, as well as, antibodies extracted from immunized serum that was depleted of the antibodies by pre-incubation with phenylalanine fibrils, and heterozygous pah$^{enu2}$ mice brain tissue stained with anti-Phe antibodies (FIGS. 7A-I).

Next, the present inventors examined the presence of phenylalanine fibrils in brain tissue of PKU patient. Histological co-staining was performed with anti-Phe fibrils antibodies and Congo red. As shown in FIGS. 3J-Q, evidence was found for the presence of phenylalanine deposition in the patient using co-staining: immunostaining (FIG. 3J-L) and Congo red staining (FIGS. 3N-Q). The control sample in FIGS. 3M and 3Q exhibit the same brain tissue location co-stained with pre-immune serum and Congo red respectively. The Congo red shows positive staining (FIG. 3Q), however the pre-immune serum did not recognize this area (FIG. 3M). These finding demonstrate the specificity of the anti-Phe fibrils antibodies. The phenylalanine assemblies' co-staining was mainly detected in the parietal cortex, which was previously suggested to be involved in the pathology of PKU in a rat model, in terms of changes in the structural organization of the cortex and decreased number of dendritic processes. Thus, the phenylalanine assemblies are not only a clear supramolecular entity, but one that is most relevant to the disease as determined by the mice model experiments.

In summary, the current study suggests a new paradigm to explain the pathology of PKU and suggest novel routes for potential therapy. Our study indicates, for the first time, the ability of the phenylalanine to form well-ordered fibrillar assemblies at the nano-scale. These assemblies are not irregular aggregates as they have typical fibrillar morphology, characteristic birefringence, ThT and Congo red fluorescence pattern and, above all, clear electron diffraction pattern. In all of these aspects, these fibrils highly resemble the properties of amyloid assemblies that are related to numerous pathological disorders. The formed structures are not only ordered as amyloid fibrils but also have strong and clear cytotoxic activities as amyloid assemblies do (28, 29). Moreover, the formation of phenylalanine aggregates could be detected in the brain of PKU model mice using anti-phenylalanine fibrils antibodies. These findings suggest that PKU is closely related to the family of amyloid-related diseases and might have similar etiology. The formation of highly-ordered fibrils at high phenylalanine concentrations resembles not only the process of amyloid formation but also the pathological processes in other diseases such as Gout disease. In Gout patients, mono-sodium urate monohydrate, at high serum levels, form crystal structures that accumulate in the joints. An acute inflammatory response is triggered by the appearance of these microscopic crystals that are formed by a process of self-assembly (30). This represents another case in which a small molecule can form ordered crystalline structures by self-assembly that execute clear and specific toxic effect. Moreover, the phenylalanine fibrils represent a distinct immunological entity as amyloid assemblies do, and many concepts and experimental studies that are used for the development of immunological treatment for amyloid diseases may also be used in the this case (24, 25).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. W. B. Hanley, *Am. J. Med.* 117, 590 (2004).
2. R. Surtees, N. Blau, *Eur. J. Pediatr.* 159, 109 (2000).
3. G. A. Jervis, E. J. Drejza, *Clinica Chimica Acta* 13, 435 (1966).
4. T. B. Choi, W. M. Pardridge, *J. Biol. Chem.* 261, 6536 (1986).
5. W. Krause et al., *J. Clin. Invest.* 75 (1985).
6. F. Chiti, C. M. Dobson, *Annu. Rev. Biochem.* 75, 333 (2006).
7. M. Sunde, C. C. Blake, *Q. Rev. Biophys.* 31, 1 (1998).
8. A. P. Pawar et al., *J. Mol. Biol.* 350, 379 (2005).
9. J. D. Sipe, A. S. Cohen, *J. Struct. Biol.* 130, 88 (2000).
10. F. E. Cohen, J. W. Kelly, *Nature* 426, 905 (2003).
11. H. Inouye, D. Sharma, W. J. Goux, D. A. Kirschner, *Biophys. J.* 90, 1774 (2006).
12. E. Gazit, *FASEB J.* 16, 77 (2002).
13. R. Azriel, E. Gazit, *J. Biol. Chem.* 276, 34156 (2001).
14. E. Gazit, *Bioinformatics* 18, 880 (2002).
15. O. S. Makin, L. C. Serpell, *FEBS J.* 272, 5950 (2005).
16. E. Gazit, *FASEB J.* 16, 77 (2002).
17. M. Reches, Y. Porat, E. Gazit, *J. Biol. Chem.* 277, 35475 (2002).
18. M. Reches, E. Gazit, *Science* 300, 625 (2003).
19. L. O. Tjernberg et al., *J. Biol. Chem.* 271, 8545 (1996).
20. M. A. Findeis et al., *Biochemistry* 38, 6791 (1999).
21. C. Soto et al., *Nat. Med.* 4, 822 (1998).
22. F. Horster et al., *Pediatrics Research* 59, 544 (2006).
23. O. S. Makin, E. Atkins, P. Sikorski, J. Johansson, L. C. Serpell, *Proc. Natl. Acad. Sci. U.S.A.* 102, 315 (2005).
24. B. Solomon, *Expert Opin. Investig. Drugs* 16, 819 (2007).
25. D. Schenk et al., *Nature* 400, 173 (1999).
26. A. Shedlovsky, J. D. McDonald, D. Symula, W. F. Dove, *Genetics* 134, 1205 (1993).
27. V. Gazit, R. Ben-Abraham, C. G. Pick, Y. Katz, *Behav Brain Res* 143, 1 (Jul. 14, 2003).
28. H. A. Lashuel, D. Hartley, B. M. Petre, T. Walz, P. T. Lansbury, *Nature* 418, 291 (2002).
29. M. Bucciantini et al., *Nature* 416, 507 (2002).
30. E. Pascual, F. Sivera, *Curr. Opin. Rheumatol.* 19 (2007).

What is claimed is:

1. A method of diagnosing Phenylketonuria (PKU) in a subject in need thereof, the method comprising detecting phenylalanine fibrils in a tissue of the subject, wherein a presence or level above a predetermined threshold of said phenylalanine fibrils in said tissue, is indicative of PKU in the subject.

2. The method of claim 1, wherein said detecting is effected using an isolated antibody which specifically binds to fibrils consisting of phenylalanine.

3. The method of claim 1, wherein said detecting is effected with a dye.

4. The method of claim 3, wherein said dye is selected from the group consisting of Congo red and ThT.

* * * * *